(12) United States Patent
Gordon et al.

(10) Patent No.: US 7,814,635 B2
(45) Date of Patent: Oct. 19, 2010

(54) METHOD OF MAKING A TISSUE SHAPING DEVICE

(75) Inventors: Lucas Gordon, Issaquah, WA (US); Mark L. Mathis, Fremont, CA (US); Nathan Aronson, Seattle, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 1111 days.

(21) Appl. No.: 11/383,115

(22) Filed: May 12, 2006

(65) Prior Publication Data

US 2006/0191121 A1    Aug. 31, 2006

Related U.S. Application Data

(62) Division of application No. 10/742,742, filed on Dec. 19, 2003.

(51) Int. Cl.
*B23P 11/00* (2006.01)
*A61F 2/24* (2006.01)

(52) U.S. Cl. .......................... 29/428; 29/557; 623/2.36; 623/2.37

(58) Field of Classification Search .................. 29/557; 623/2.36, 2.37, 2.38
See application file for complete search history.

(56) References Cited

U.S. PATENT DOCUMENTS

| | | | |
|---|---|---|---|
| 3,974,526 A | 8/1976 | Dardik et al. | |
| 3,995,623 A | 12/1976 | Black et al. | |
| 4,055,861 A | 11/1977 | Carpentier et al. | |
| 4,164,046 A | 8/1979 | Cooley | |
| 4,485,816 A | 12/1984 | Krumme | |
| 4,550,870 A | 11/1985 | Krumme et al. | |
| 4,588,395 A | 5/1986 | Lemelson | |
| 4,830,023 A | 5/1989 | de Toledo et al. | |
| 5,061,277 A | 10/1991 | Carpentier et al. | |
| 5,099,838 A | 3/1992 | Bardy | |
| 5,104,404 A | 4/1992 | Wolff | |
| 5,250,071 A | 10/1993 | Palermo | |
| 5,261,916 A | 11/1993 | Engelson | |

(Continued)

FOREIGN PATENT DOCUMENTS

EP    0893133    1/1999

(Continued)

OTHER PUBLICATIONS

Mathis et al; U.S. Appl. No. 11/963,417 entitled "Device and method for modifying the shape of a body organ," filed Dec. 21, 2007.

(Continued)

*Primary Examiner*—Jermie E Cozart
(74) *Attorney, Agent, or Firm*—Shay Glenn LLP

(57) ABSTRACT

A tissue shaping device adapted to be deployed in a vessel to reshape tissue adjacent to the vessel. In some embodiments the device includes first and second anchors and a connector disposed between the first and second anchors, with the connector being integral with at least a portion of the first anchor. The invention is also a method of making a tissue shaping device including the steps of removing material from a blank to form a connector and an integral anchor portion; and attaching a non-integral anchor portion to the integral anchor portion.

6 Claims, 17 Drawing Sheets

U.S. PATENT DOCUMENTS

| | | |
|---|---|---|
| 5,265,601 A | 11/1993 | Mehra |
| 5,350,420 A | 9/1994 | Cosgrove et al. |
| 5,433,727 A | 7/1995 | Sideris |
| 5,441,515 A | 8/1995 | Khosravi et al. |
| 5,449,373 A | 9/1995 | Pinchasik et al. |
| 5,454,365 A | 10/1995 | Bonutti |
| 5,458,615 A | 10/1995 | Klemm et al. |
| 5,474,557 A | 12/1995 | Mai |
| 5,507,295 A | 4/1996 | Skidmore |
| 5,507,802 A | 4/1996 | Imran |
| 5,514,161 A | 5/1996 | Limousin |
| 5,554,177 A | 9/1996 | Kieval et al. |
| 5,562,698 A | 10/1996 | Parker |
| 5,575,818 A | 11/1996 | Pinchuk |
| 5,584,867 A | 12/1996 | Limousin et al. |
| 5,601,600 A | 2/1997 | Ton |
| 5,662,703 A | 9/1997 | Yurek et al. |
| 5,676,671 A | 10/1997 | Inoue |
| 5,733,325 A | 3/1998 | Robinson et al. |
| 5,741,297 A | 4/1998 | Simon |
| 5,752,969 A | 5/1998 | Cunci et al. |
| 5,800,519 A | 9/1998 | Sandock |
| 5,824,071 A | 10/1998 | Nelson et al. |
| 5,836,882 A | 11/1998 | Frazin |
| 5,871,501 A | 2/1999 | Leschinsky et al. |
| 5,891,193 A | 4/1999 | Robinson et al. |
| 5,895,391 A | 4/1999 | Farnholtz |
| 5,899,882 A | 5/1999 | Waksman et al. |
| 5,908,404 A | 6/1999 | Elliott |
| 5,928,258 A | 7/1999 | Khan et al. |
| 5,935,161 A | 8/1999 | Robinson et al. |
| 5,954,761 A | 9/1999 | Machek et al. |
| 5,961,545 A | 10/1999 | Lentz et al. |
| 5,978,705 A | 11/1999 | KenKnight et al. |
| 5,984,944 A | 11/1999 | Forber |
| 6,007,519 A | 12/1999 | Rosselli |
| 6,015,402 A | 1/2000 | Sahota |
| 6,022,371 A | 2/2000 | Killion |
| 6,027,517 A | 2/2000 | Crocker et al. |
| 6,053,900 A | 4/2000 | Brown et al. |
| 6,056,775 A | 5/2000 | Borghi et al. |
| 6,077,295 A | 6/2000 | Limon et al. |
| 6,077,297 A | 6/2000 | Robinson et al. |
| 6,080,182 A | 6/2000 | Shaw et al. |
| 6,086,611 A | 7/2000 | Duffy et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,171,320 B1 | 1/2001 | Monassevitch |
| 6,183,512 B1 | 2/2001 | Howanec et al. |
| 6,190,406 B1 | 2/2001 | Duerig et al. |
| 6,200,336 B1 | 3/2001 | Pavcnik et al. |
| 6,210,432 B1 | 4/2001 | Solem et al. |
| 6,228,098 B1 | 5/2001 | Kayan et al. |
| 6,241,757 B1 | 6/2001 | An et al. |
| 6,254,628 B1 | 7/2001 | Wallace et al. |
| 6,267,783 B1 | 7/2001 | Letendre et al. |
| 6,275,730 B1 | 8/2001 | KenKnight et al. |
| 6,306,141 B1 | 10/2001 | Jervis |
| 6,312,446 B1 | 11/2001 | Huebsch et al. |
| 6,334,864 B1 | 1/2002 | Amplatz et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,395,017 B1 | 5/2002 | Dwyer et al. |
| 6,402,781 B1 | 6/2002 | Langberg et al. |
| 6,419,696 B1 | 7/2002 | Ortiz et al. |
| 6,442,427 B1 | 8/2002 | Boute et al. |
| 6,464,720 B2 | 10/2002 | Boatman et al. |
| 6,503,271 B2 | 1/2003 | Duerig et al. |
| 6,537,314 B2 | 3/2003 | Langberg et al. |
| 6,562,067 B2 | 5/2003 | Mathis |
| 6,569,198 B1 | 5/2003 | Wilson et al. |
| 6,589,208 B2 | 7/2003 | Ewers et al. |
| 6,599,314 B2 | 7/2003 | Mathis et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | St. Goar et al. |
| 6,629,994 B2 | 10/2003 | Gomez et al. |
| 6,643,546 B2 | 11/2003 | Mathis et al. |
| 6,648,881 B2 | 11/2003 | KenKnight et al. |
| 6,652,538 B2 | 11/2003 | Kayan et al. |
| 6,656,221 B2 | 12/2003 | Taylor et al. |
| 6,676,702 B2 | 1/2004 | Mathis |
| 6,689,164 B1 | 2/2004 | Seguin |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,721,598 B1 | 4/2004 | Helland et al. |
| 6,723,038 B1 | 4/2004 | Schroeder et al. |
| 6,733,521 B2 | 5/2004 | Chobotov et al. |
| 6,743,219 B1 | 6/2004 | Dwyer et al. |
| 6,764,510 B2 | 7/2004 | Vidlund et al. |
| 6,773,446 B1 | 8/2004 | Dwyer et al. |
| 6,776,784 B2 | 8/2004 | Ginn |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,800,090 B2 | 10/2004 | Alferness et al. |
| 6,805,128 B1 | 10/2004 | Pless et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,827,690 B2 | 12/2004 | Bardy |
| 6,881,220 B2 | 4/2005 | Edwin et al. |
| 6,899,734 B2 | 5/2005 | Castro et al. |
| 6,908,478 B2 | 6/2005 | Alferness et al. |
| 6,935,404 B2 | 8/2005 | Duerig et al. |
| 6,949,122 B2 | 9/2005 | Adams et al. |
| 6,960,229 B2 | 11/2005 | Mathis et al. |
| 6,964,683 B2 | 11/2005 | Kowalsky et al. |
| 6,966,926 B2 | 11/2005 | Mathis |
| 6,976,995 B2 | 12/2005 | Mathis et al. |
| 7,152,605 B2 | 12/2006 | Khairkhahan et al. |
| 7,175,653 B2 | 2/2007 | Gaber |
| 2001/0018611 A1 | 8/2001 | Solem et al. |
| 2001/0041899 A1 | 11/2001 | Foster |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0087173 A1 | 7/2002 | Alferness et al. |
| 2002/0095167 A1 | 7/2002 | Liddicoat et al. |
| 2002/0138044 A1 | 9/2002 | Streeter et al. |
| 2002/0151961 A1 | 10/2002 | Lashinski et al. |
| 2002/0156526 A1 | 10/2002 | Hlavka et al. |
| 2002/0161377 A1 | 10/2002 | Rabkin et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0018358 A1 | 1/2003 | Saadat |
| 2003/0040771 A1 | 2/2003 | Hyodoh et al. |
| 2003/0069636 A1 | 4/2003 | Solem et al. |
| 2003/0078465 A1 | 4/2003 | Pai et al. |

| Publication No. | Date | Inventor |
|---|---|---|
| 2003/0078654 A1 | 4/2003 | Taylor et al. |
| 2003/0083613 A1 | 5/2003 | Schaer |
| 2003/0088305 A1 | 5/2003 | Van Schie et al. |
| 2003/0130730 A1 | 7/2003 | Cohn et al. |
| 2003/0135267 A1 | 7/2003 | Solem et al. |
| 2003/0171776 A1 | 9/2003 | Adams et al. |
| 2003/0236569 A1 | 12/2003 | Mathis et al. |
| 2004/0010305 A1 | 1/2004 | Alferness et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0111095 A1 | 6/2004 | Gordon et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220654 A1 | 11/2004 | Mathis et al. |
| 2004/0220657 A1 | 11/2004 | Nieminen et al. |
| 2004/0249452 A1 | 12/2004 | Adams et al. |
| 2004/0260342 A1 | 12/2004 | Vargas et al. |
| 2005/0004667 A1 | 1/2005 | Swinford et al. |
| 2005/0010240 A1 | 1/2005 | Mathis et al. |
| 2005/0021121 A1 | 1/2005 | Reuter et al. |
| 2005/0027351 A1 | 2/2005 | Reuter et al. |
| 2005/0027353 A1 | 2/2005 | Alferness et al. |
| 2005/0033419 A1 | 2/2005 | Alferness et al. |
| 2005/0038507 A1 | 2/2005 | Alferness et al. |
| 2005/0060030 A1 | 3/2005 | Lashinski et al. |
| 2005/0065598 A1 | 3/2005 | Mathis et al. |
| 2005/0085903 A1 | 4/2005 | Lau |
| 2005/0096666 A1 | 5/2005 | Gordon et al. |
| 2005/0096740 A1 | 5/2005 | Langberg et al. |
| 2005/0107810 A1 | 5/2005 | Morales et al. |
| 2005/0119673 A1 | 6/2005 | Gordon et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137685 A1 | 6/2005 | Nieminen et al. |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0177228 A1 | 8/2005 | Solem et al. |
| 2005/0187619 A1 | 8/2005 | Mathis et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0261704 A1 | 11/2005 | Mathis |
| 2005/0272969 A1 | 12/2005 | Alferness et al. |
| 2006/0020335 A1 | 1/2006 | Kowalsky et al. |
| 2006/0030882 A1 | 2/2006 | Adams et al. |
| 2006/0041305 A1 | 2/2006 | Lauterjung |
| 2006/0116758 A1 | 6/2006 | Swinford et al. |
| 2006/0142854 A1 | 6/2006 | Alferness et al. |
| 2006/0161169 A1 | 7/2006 | Nieminen et al. |
| 2006/0167544 A1 | 7/2006 | Nieminen et al. |
| 2006/0173536 A1 | 8/2006 | Mathis et al. |
| 2006/0271174 A1 | 11/2006 | Nieminen et al. |
| 2006/0276891 A1 | 12/2006 | Nieminen et al. |
| 2007/0055293 A1 | 3/2007 | Alferness et al. |
| 2007/0066879 A1 | 3/2007 | Mathis et al. |

FOREIGN PATENT DOCUMENTS

| | | |
|---|---|---|
| EP | 0903110 A1 | 3/1999 |
| EP | 0968688 A1 | 1/2000 |
| EP | 1050274 A1 | 11/2000 |
| EP | 1095634 A2 | 5/2001 |
| GB | 0741604 | 12/1955 |
| JP | 2754067 | 3/1998 |
| JP | 2000-308652 | 11/2000 |
| JP | 2001-503291 | 3/2001 |
| JP | 2003-503101 | 1/2003 |
| JP | 2003-521310 | 7/2003 |
| WO | WO 98/56435 A1 | 12/1998 |
| WO | WO 00/44313 A1 | 8/2000 |
| WO | WO 00/60995 A2 | 10/2000 |
| WO | WO 00/74603 A1 | 12/2000 |
| WO | WO 01/00111 A1 | 1/2001 |
| WO | WO 01/19292 A1 | 3/2001 |
| WO | WO 01/50985 A1 | 7/2001 |
| WO | WO 01/54618 A1 | 8/2001 |
| WO | WO 01/87180 A2 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/19951 A1 | 3/2002 |
| WO | WO 02/34118 A2 | 5/2002 |
| WO | WO 02/47539 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/015611 A2 | 2/2003 |
| WO | WO 03/037171 A2 | 5/2003 |
| WO | WO 03/049647 A1 | 6/2003 |
| WO | WO 03049648 A2 | 6/2003 |
| WO | WO 03/055417 A1 | 7/2003 |
| WO | WO 03/059198 A2 | 7/2003 |
| WO | WO 03/063735 A2 | 8/2003 |
| WO | WO 2004/045463 A2 | 6/2004 |
| WO | WO 2004/084746 | 10/2004 |
| WO | WO 2005/046531 | 5/2005 |

OTHER PUBLICATIONS

Mathis et al.; U.S. Appl. No. 12/016,054 entitled "Fixed anchor and pull mitral valve device and method," filed Jan. 17, 2008.

Gordon et al.; U.S. Appl. No. 11/971,174 entitled "Medical device delivery system," filed Jan. 8, 2008.

Nieminen et al; U.S. Appl. No. 12/060,781 entitled "Tissue shaping device," filed Apr. 1, 2008.

Pai, Suresh; U.S. Appl. No. 60/329,694 entitled "Percutaneous cardiac support structures and deployment means," filed Oct. 16, 2001.

Mathis, et al; U.S. Appl. No. 11/279,352, entitled "Mitral Valve Annuloplasty Device with Vena Cava Anchor," filed Apr. 11, 2006.

Mathis, Mark; U.S. Appl. No. 11/655,710, entitled "Mitral Valve Device Using Conditioned Shape Memory Alloy," filed Jan. 18, 2007.

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Heartsite.com. Echocardiogram, 1999; p. 1-4. A.S.M. Systems Inc. Available at: http://www.heartsite.com/html/echocardiogram.html. Accessed Jul. 1, 2005.

Papageorgiou, P., et al. Coronary Sinus Pacing Prevents Induction of Atrial Fibrillation. Circulation. 1997; 96(6): 1893-1898.

Yamanouchi, et al.; Activation Mapping from the coronary sinus may be limited by anatomic variations; vol. 21 pp. 2522-2526; Nov. 1998.

Mathis et al., U.S. Appl. No. 11/782,490 entitled "Device and method for modifying the shape of a body organ, " filed Jul. 24, 2007.

Mathis et al., U.S. Appl. No. 11/782,508, entitled "Device and method for modifying the shape of a body organ," filed Jul. 24, 2007.

Mathis et al., U.S. Appl. No. 11/782,527 entitled "Device and method for modifying the shape of a body organ," filed Jul. 24, 2007.

Hayner et al.; U.S. Appl. No. 12/189,527 entitled "Catheter cutting tool," filed Aug. 11, 2008.

El-Maasarany et al.; The coronary sinus conduit function: Anatomical study (relationship to adjacent structures); http://europace.oxfordjournals.org/cge/content/full/7/5/475.

Reuter et al.; U.S. Appl. No. 12/642,525 entitled "Adjustable Height Focal Tissue Deflector," filed Dec. 18, 2009.

Alferness et al.; U.S. Appl. No. 12/719,758 entitled "Device and Method for Modifying the Shape of a Body Organ," filed Mar. 8, 2010.

Pijls et al.; Measurement of fractional flow reserve to assess the functional severity of coronary-artery stenoses; The New England J. of Med.; vol. 334; No. 26; pp. 1703-1708; Jun. 27, 1996.

METHOD OF MAKING A TISSUE SHAPING DEVICE

CROSS-REFERENCE

This application is a divisional application of Ser. No. 10/742,742, filed Dec. 19, 2003, which is incorporated herein by reference in its entirety, and to which application we claim priority under 35 USC §121.

BACKGROUND OF THE INVENTION

This invention relates generally to devices and methods for shaping tissue by deploying one or more devices in body lumens adjacent to the tissue. One particular application of the invention relates to a treatment for mitral valve regurgitation through deployment of a tissue shaping device in the patient's coronary sinus or great cardiac vein.

The mitral valve is a portion of the heart that is located between the chambers of the left atrium and the left ventricle. When the left ventricle contracts to pump blood throughout the body, the mitral valve closes to prevent the blood being pumped back into the left atrium. In some patients, whether due to genetic malformation, disease or injury, the mitral valve fails to close properly causing a condition known as regurgitation, whereby blood is pumped into the atrium upon each contraction of the heart muscle. Regurgitation is a serious, often rapidly deteriorating, condition that reduces circulatory efficiency and must be corrected.

Two of the more common techniques for restoring the function of a damaged mitral valve are to surgically replace the valve with a mechanical valve or to suture a flexible ring around the valve to support it. Each of these procedures is highly invasive because access to the heart is obtained through an opening in the patient's chest. Patients with mitral valve regurgitation are often relatively frail thereby increasing the risks associated with such an operation.

One less invasive approach for aiding the closure of the mitral valve involves the placement of a tissue shaping device in the cardiac sinus and vessel that passes adjacent the mitral valve. The tissue shaping device is designed to push the vessel and surrounding tissue against the valve to aid its closure. This technique has the advantage over other methods of mitral valve repair because it can be performed percutaneously without opening the chest wall. Examples of such devices are shown in U.S. patent application Ser. No. 10/142,637, "Body Lumen Device Anchor, Device and Assembly" filed May 8, 2002; U.S. patent application Ser. No. 10/331,143, "System and Method to Effect the Mitral Valve Annulus of a Heart" filed Dec. 26, 2002; and U.S. patent application Ser. No. 10/429,172, "Device and Method for Modifying the Shape of a Body Organ," filed May 2, 2003. The disclosures of these patent applications are incorporated herein by reference.

When deploying a tissue shaping device in a vein or artery to modify adjacent tissue, care must be taken to avoid constricting nearby arteries. For example, when treating mitral valve regurgitation, a tissue shaping device may be deployed in the coronary sinus to modify the shape of the adjacent mitral valve annulus. Coronary arteries such as the circumflex artery may cross between the coronary sinus and the heart, however, raising the danger that deployment of the support may limit perfusion to a portion of the heart by constricting one of those arteries. See, e.g., the following applications, the disclosures of which are incorporated herein by reference: U.S. patent application Ser. No. 09/855,945, "Mitral Valve Therapy Device, System and Method," filed May 14, 2001 and published Nov. 14, 2002, as US 2002/0169504 A1; U.S. patent application Ser. No. 09/855,946, "Mitral Valve Therapy Assembly and Method," filed May 14, 2001 and published Nov. 14, 2002, as US 2002/0169502 A1; and U.S. patent application Ser. No. 10/003,910, "Focused Compression Mitral Valve Device and Method" filed Nov. 1, 2001. It is therefore advisable to monitor cardiac perfusion during and after such mitral valve regurgitation therapy. See, e.g., U.S. patent application Ser. No. 10/366,585, "Method of Implanting a Mitral Valve Therapy Device," filed Feb. 12, 2003, the disclosure of which is incorporated herein by reference.

BRIEF SUMMARY OF THE INVENTION

The anatomy of the heart and its surrounding vessels varies from patient to patient. For example, the location of the circumflex artery and other key arteries with respect to the coronary sinus can vary. Specifically, the distance along the coronary sinus from the ostium to the crossing point with the circumflex artery can vary from patient to patient. In addition, the diameter and length of the coronary sinus can vary from patient to patient.

We have invented a tissue shaping device, a set of tissue shaping devices and a method that maximize the therapeutic effect (i.e., reduction of mitral valve regurgitation) while minimizing adverse effects, such as an unacceptable constriction of the circumflex artery or other coronary arteries. The tissue shaping device, set of devices and method of this invention enable the user to adapt the therapy to the patient's anatomy.

One aspect of the invention provides a tissue shaping device adapted to be deployed in a vessel to reshape tissue adjacent to the vessel, the device including first and second anchors and a connector disposed between the first and second anchors, the connector being integral with at least a portion of the first anchor. In some embodiments the first anchor has a flexible wire and a crimp holding a portion of the flexible wire, with the crimp being optionally integral with the connector. The connector may have a semicircular cross-section with a radius substantially equal to a crimp radius.

In some embodiments the device's first and second anchors each have a flexible wire and a crimp holding a portion of the flexible wire, and the first anchor crimp and the second anchor crimp may be integral with the connector.

Another aspect of the invention provides a method of making a tissue shaping device, the method including the steps of: removing material from a blank to form a connector and an integral anchor portion; and attaching a non-integral anchor portion to the integral anchor portion. In embodiments in which the integral anchor portion includes a crimp tube and the non-integral portion includes a flexible wire, the method may further include the step of disposing a portion of the flexible wire in the crimp tube. In embodiments in which the blank has a substantially cylindrical cross-section, the removing step may include the step of removing a portion of the cylinder to leave a connector having a substantially semicircular cross-section.

In embodiments in which the integral anchor portion is a first integral anchor portion, the removing step may further include the step of removing material from the blank to form a second integral anchor portion, with the connector being disposed between the first integral anchor portion and the second integral anchor portion. In embodiments in which the first and second anchor portions each have a crimp tube and the non-integral anchor portion includes a flexible wire, the method may further include the step of disposing a portion of the flexible wire in the first anchor crimp tube.

In embodiments in which the non-integral anchor portion is a first non-integral anchor portion, the method may further include the step of attaching a second non-integral anchor portion to the second integral anchor portion. In some embodiments the first and second integral anchor portions each have a crimp tube and the first and second non-integral anchor portions each include a flexible wire, with the method further including the steps of disposing a portion of the first anchor flexible wire in the first anchor crimp tube and disposing a portion of the second anchor flexible wire in the second anchor crimp tube.

The invention will be described in more detail below with reference to the drawings.

DETAILED DESCRIPTION OF THE INVENTION

Figure 1:
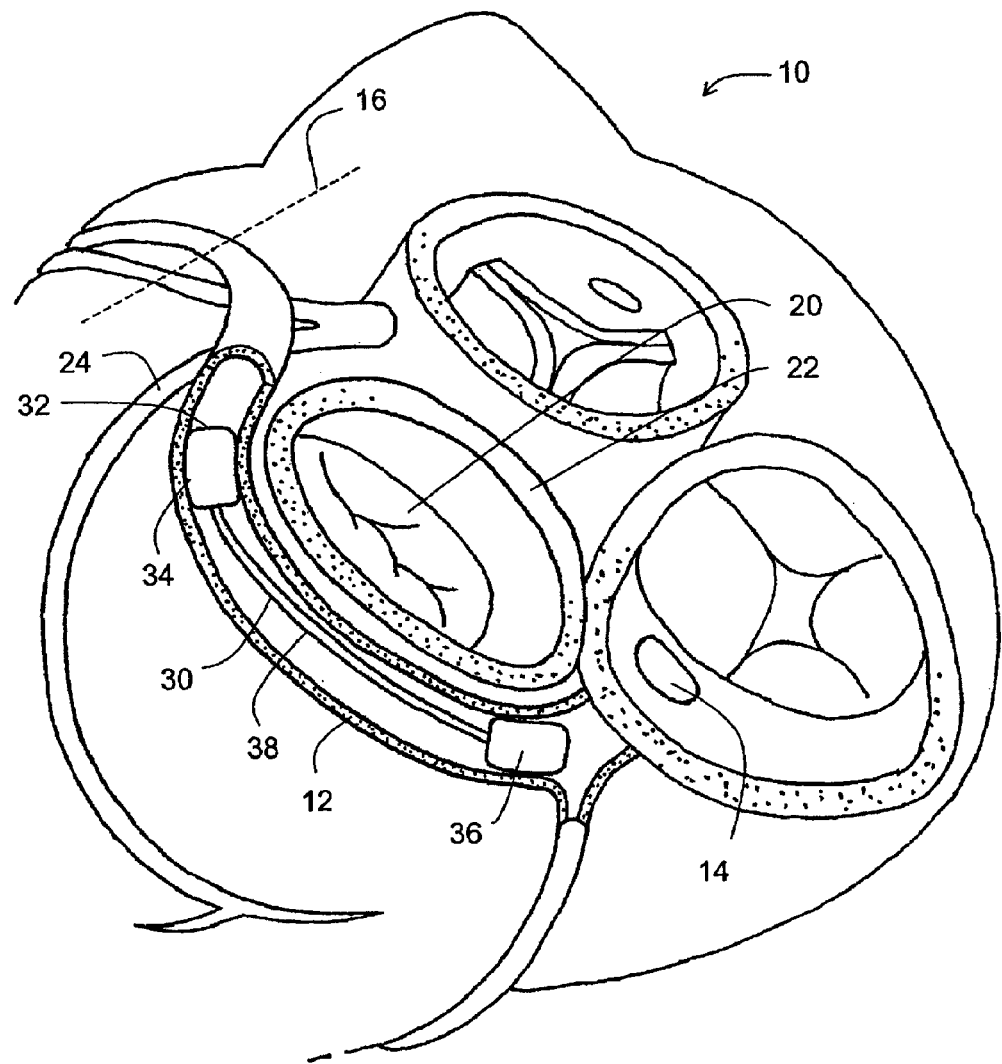
FIG. 1 is a schematic view of a tissue shaping device according to a preferred embodiment as deployed within a coronary sinus.

FIG. 1 shows a partial view of a human heart 10 and some surrounding anatomical structures. The main coronary venous vessel is the coronary sinus 12, defined as starting at the ostium 14 or opening to the right atrium and extending through the great cardiac vein to the anterior interventricular ("AIV") sulcus or groove 16. Also shown is the mitral valve 20 surrounded by the mitral valve annulus 22 and adjacent to at least a portion of the coronary sinus 12. The circumflex artery 24 shown in FIG. 1 passes between the coronary sinus 12 and the heart. The relative size and location of each of these structures vary from person to person.

Disposed within the coronary sinus 12 is a tissue shaping device 30. As shown in FIG. 1, the distal end 32 of device 30 is disposed proximal to circumflex artery 24 to reshape the adjacent mitral valve annulus 22 and thereby reduce mitral valve regurgitation. As shown in FIG. 1, device 30 has a distal anchor 34, a proximal anchor 36 and a connector 38.

In the embodiment of FIG. 1, proximal anchor 36 is deployed completely within the coronary sinus. In the alternative embodiment shown in FIG. 2, proximal anchor is deployed at least partially outside the coronary sinus.

Figure 3:
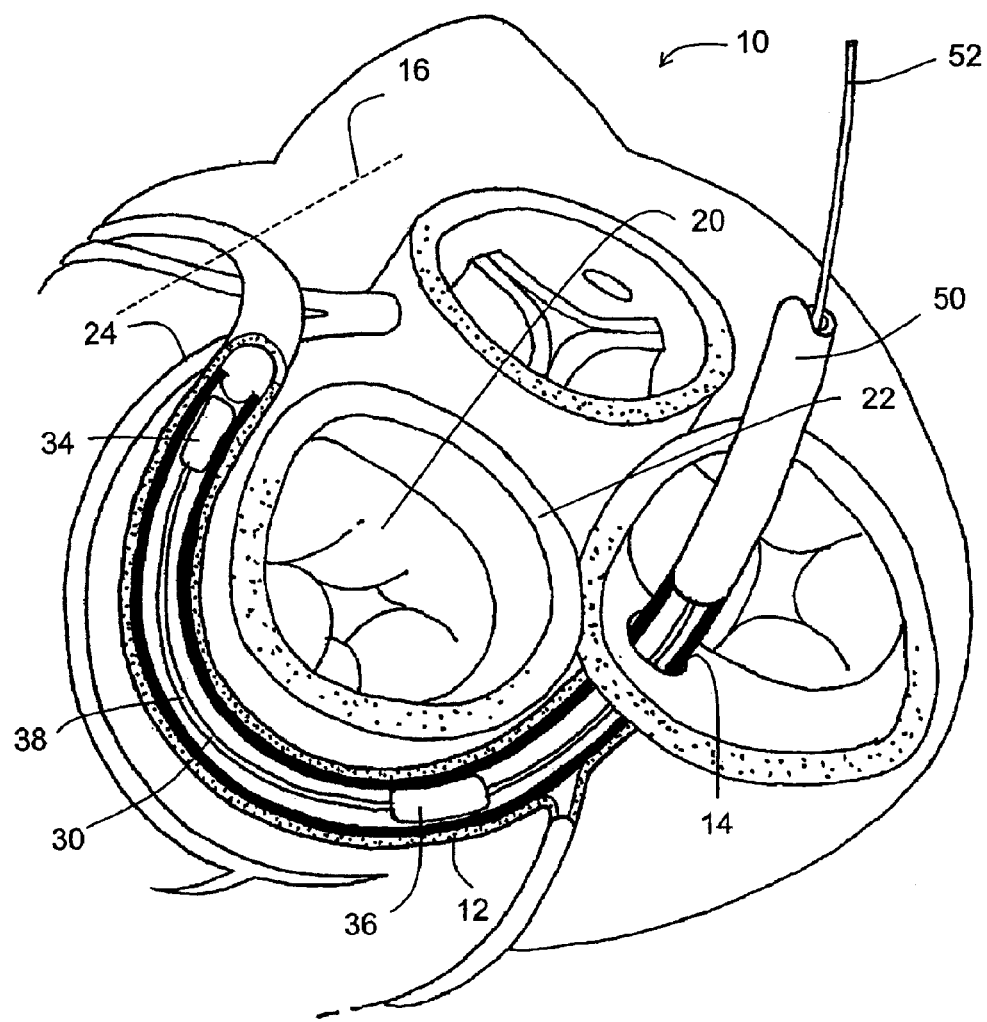
FIG. 3 is a schematic view of a tissue shaping device being delivered to a coronary sinus within a catheter.

FIGS. 3-6 show a method according to this invention. As shown in FIG. 3, a catheter 50 is maneuvered in a manner known in the art through the ostium 14 into coronary sinus 12. In order to be navigable through the patient's venous system, catheter 50 preferably has an outer diameter no greater than ten french, most preferably with an outer diameter no more than nine french. Disposed within catheter 50 is device 30 in an unexpanded configuration, and extending back through catheter 50 from device 30 to the exterior of the patient is a tether or control wire 52. In some embodiments, control wire 52 may include multiple tether and control wire elements, such as those described in U.S. patent application Ser. No. 10/331,143.

According to one preferred embodiment, the device is deployed as far distally as possible without applying substantial compressive force on the circumflex or other major coronary artery. Thus, the distal end of catheter 50 is disposed at a distal anchor location proximal of the crossover point between the circumflex artery 24 and the coronary sinus 12 as shown in FIG. 3. At this point, catheter 50 is withdrawn proximally while device 30 is held stationary by control wire 52 to uncover distal anchor 34 at the distal anchor location within coronary sinus 12. Alternatively, the catheter may be held stationary while device 30 is advanced distally to uncover the distal anchor.

Figure 4:
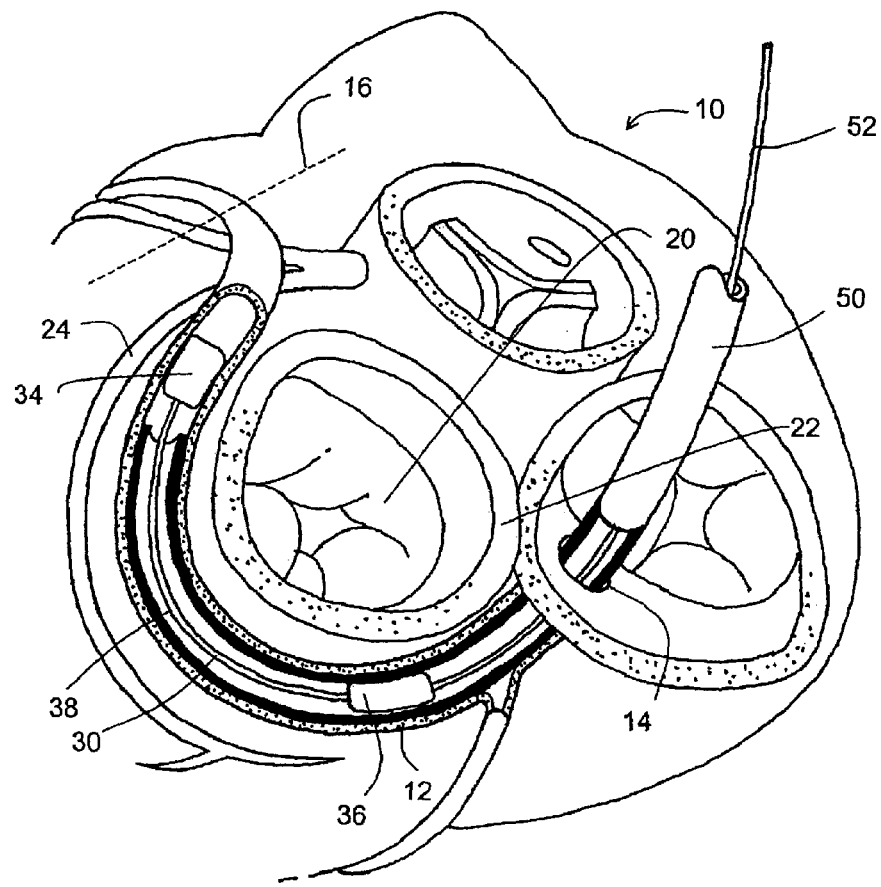
FIG. 4 is a schematic view of a partially deployed tissue shaping device within a coronary sinus.

Distal anchor 34 is either a self-expanding anchor or an actuatable anchor or a combination self-expanding and actuatable anchor. Once uncovered, distal anchor 34 self-expands, or is expanded through the application of an actuation force (such as a force transmitted through control wire 52), to engage the inner wall of coronary sinus 12, as shown in FIG. 4. The distal anchor's anchoring force, i.e., the force with which the distal anchor resists moving in response to a proximally-directed force, must be sufficient not only to maintain the device's position within the coronary sinus but also to enable the device to be used to reshape adjacent tissue in a manner such as that described below. In a preferred embodiment, distal anchor 34 engages the coronary sinus wall to provide an anchoring force of at least one pound, most preferably an anchoring force of at least two pounds. The anchor's expansion energy to supply the anchoring force comes from strain energy stored in the anchor due to its compression for catheter delivery, from an actuation force, or a combination of both, depending on anchor design.

Figure 5:
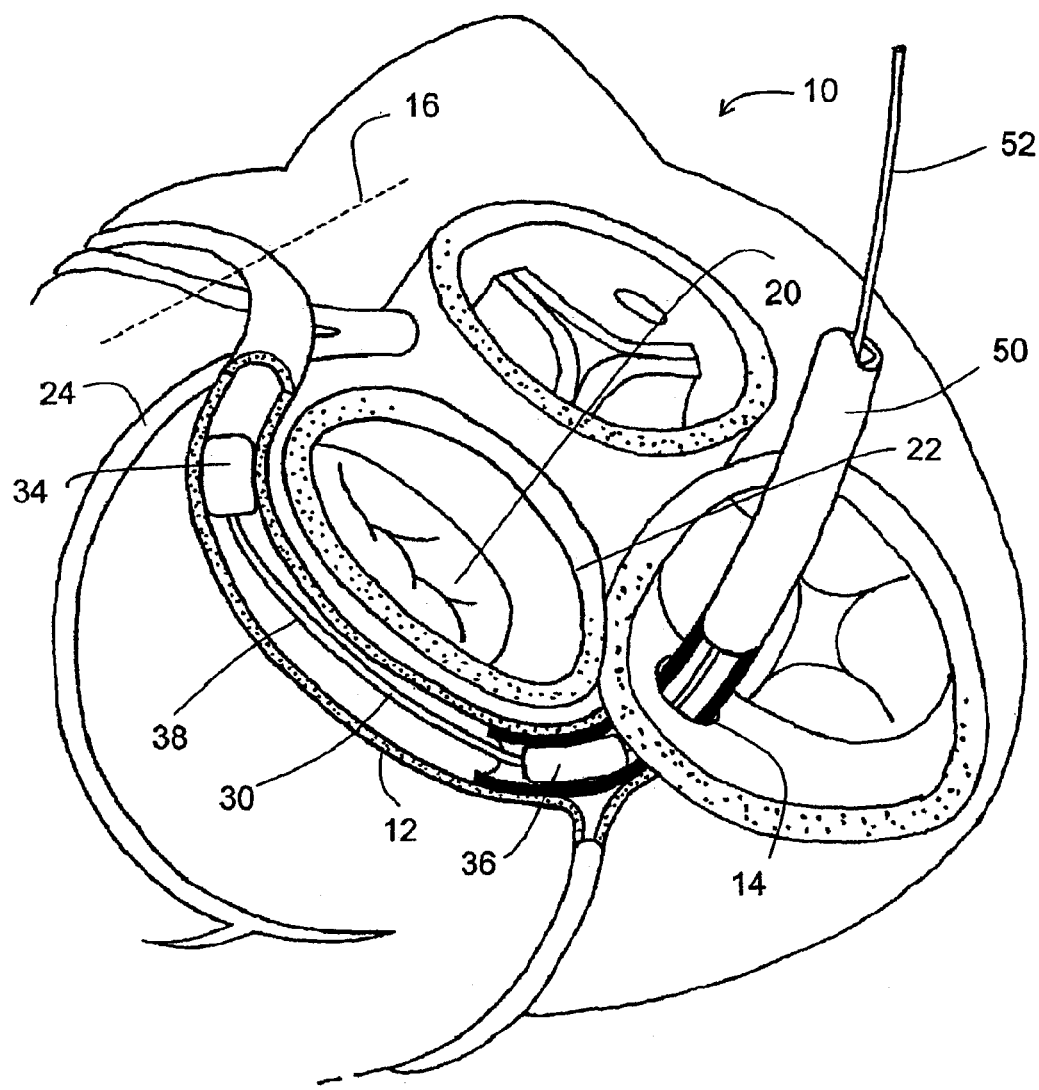
FIG. 5 is a schematic view of a partially deployed and cinched tissue shaping device within a coronary sinus.

While device 30 is held in place by the anchoring force of distal anchor 34, catheter 50 is withdrawn further proximally to a point just distal of proximal anchor 36, as shown in FIG. 5. A proximally directed force is then exerted on distal anchor 34 by control wire 52 through connector 38. In this embodiment, the distance between the distal and proximal anchors along the connector is fixed, so the proximally directed force moves proximal anchor 36 proximally with respect to the coronary sinus while distal anchor 34 remains stationary with respect to the coronary sinus. This cinching action straightens that section of coronary sinus 12, thereby modifying its shape and the shape of the adjacent mitral valve 20, moving the mitral valve leaflets into greater coaptation and reducing mitral valve regurgitation. In some embodiments of the invention, the proximal anchor is moved proximally about 1-6 cm., most preferably at least 2 cm., in response to the proximally directed force. In other embodiments, such as embodiments in which the distance between the distal and proximal anchors is not fixed (e.g., where the connector length is variable), the proximal anchor may stay substantially stationary with respect to the coronary sinus despite the application of a proximally directed force on the distal anchor.

After the appropriate amount of reduction in mitral valve regurgitation has been achieved (as determined, e.g., by viewing doppler-enhanced echocardiograms), the proximal anchor is deployed. Other patient vital signs, such as cardiac perfusion, may also be monitored during this procedure as described in U.S. patent application Ser. No. 10/366,585.

In preferred embodiments, the proximal anchor's anchoring force, i.e., the force with which the proximal anchor resists moving in response to a distally-directed force, must be sufficient not only to maintain the device's position within the coronary sinus but also to enable the device to maintain the adjacent tissue's cinched shape. In a preferred embodiment, the proximal anchor engages the coronary sinus wall to provide an anchoring force of at least one pound, most preferably an anchoring force of at least two pounds. As with the distal anchor, the proximal anchor's expansion energy to supply the anchoring force comes from strain energy stored in the anchor due to its compression for catheter delivery, from an actuation force, or a combination of both, depending on anchor design.

In a preferred embodiment, the proximal anchor is deployed by withdrawing catheter 50 proximally to uncover proximal anchor 36, then either permitting proximal anchor 36 to self-expand, applying an actuation force to expand the anchor, or a combination of both. The control wire 52 is then detached, and catheter 50 is removed from the patient. The device location and configuration as deployed according to this method is as shown in FIG. 1.

Figure 2:
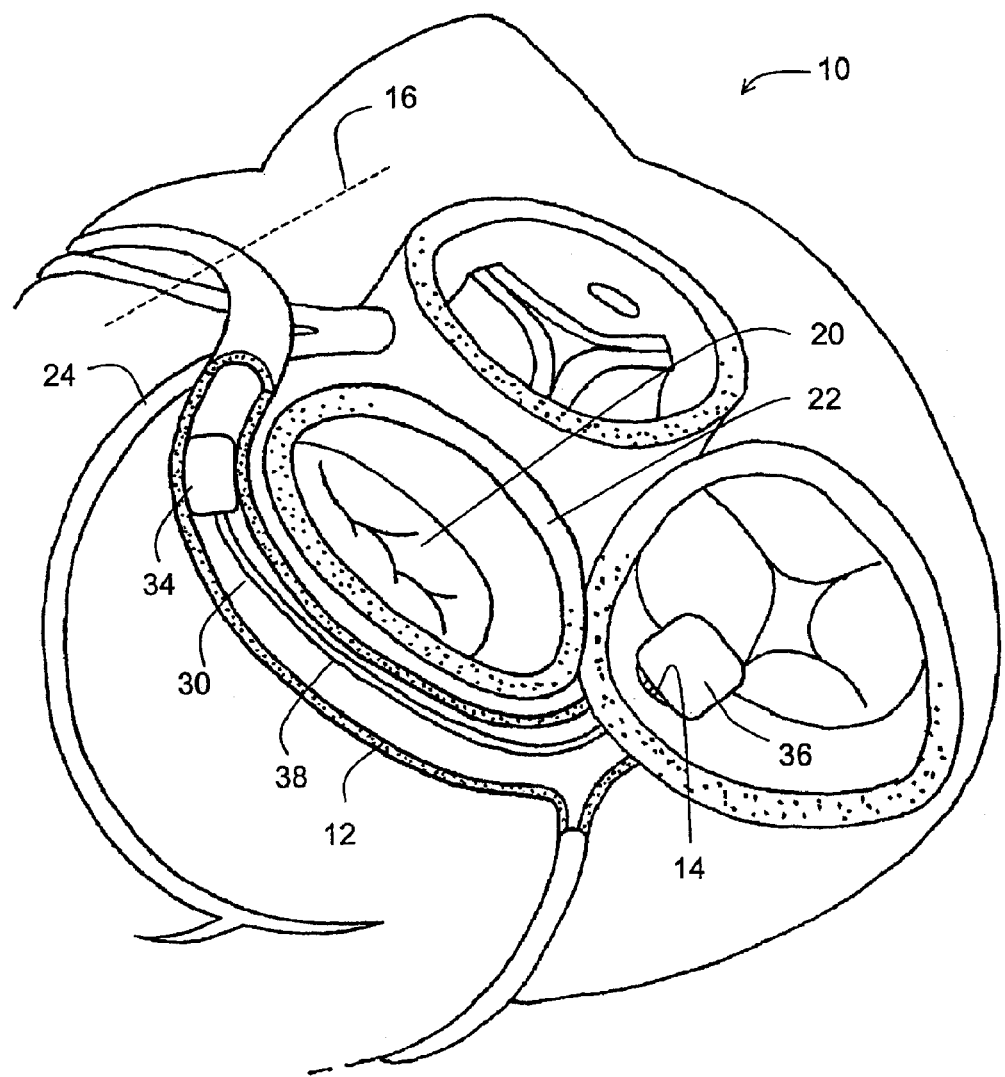
FIG. 2 is a schematic view of a tissue shaping device according to an alternative embodiment as deployed within a coronary sinus.

Alternatively, proximal anchor 36 may be deployed at least partially outside of the coronary sinus after cinching to modify the shape of the mitral valve tissue, as shown in FIG. 2. In both embodiments, because distal anchor 34 is disposed proximal to the crossover point between coronary sinus 12 and circumflex artery 24, all of the anchoring and tissue reshaping force applied to the coronary sinus by device 30 is solely proximal to the crossover point.

Figure 6:
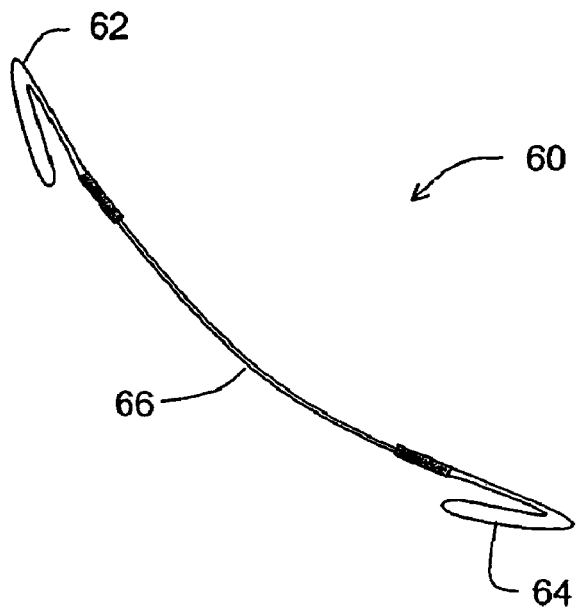
FIG. 6 is an elevational view of yet another embodiment of a tissue shaping device according to this invention.

In alternative embodiments, the proximal anchor may be deployed prior to the application of the proximally directed force to cinch the device to reshape the mitral valve tissue. One example of a device according to this embodiment is shown in FIG. 6. Device 60 includes a self-expanding distal anchor 62, a self-expanding proximal anchor 64 and a connector 66. The design of distal anchor 62 enables it to maintain its anchoring force when a proximally directed force is applied on it to cinch, while the design of proximal anchor 64 permits it to be moved proximally after deployment while resisting distal movement after cinching. Cinching after proximal anchor deployment is described in more detail in U.S. patent application Ser. No. 10/066,426, filed Jan. 30, 2002, the disclosure of which is incorporated herein by reference. In this embodiment as well, distal anchor 62 is disposed proximal to the crossover point between coronary sinus 12 and circumflex artery 24 so that all of anchoring and tissue reshaping force applied to the coronary sinus by device 30 is solely proximal to the crossover point.

It may be desirable to move and/or remove the tissue shaping device after deployment or to re-cinch after initial cinching. According to certain embodiments of the invention, therefore, the device or one of its anchors may be recaptured. For example, in the embodiment of FIG. 1, after deployment of proximal anchor 36 but prior to disengagement of control wire 52, catheter 50 may be moved distally to place proximal anchor 36 back inside catheter 50, e.g., to the configuration shown in FIG. 5. From this position, the cinching force along connector 38 may be increased or decreased, and proximal anchor 36 may then be redeployed.

Alternatively, catheter 50 may be advanced distally to recapture both proximal anchor 36 and distal anchor 34, e.g., to the configuration shown in FIG. 3. From this position, distal anchor 34 may be redeployed, a cinching force applied, and proximal anchor 36 deployed as discussed above. Also from this position, device 30 may be removed from the patient entirely by simply withdrawing the catheter from the patient.

Fluoroscopy (e.g., angiograms and venograms) may be used to determine the relative positions of the coronary sinus and the coronary arteries such as the circumflex artery, including the crossover point between the vessels and whether or not the artery is between the coronary sinus and the heart. Radiopaque dye may be injected into the coronary sinus and into the arteries in a known manner while the heart is viewed on a fluoroscope.

Figure 7:
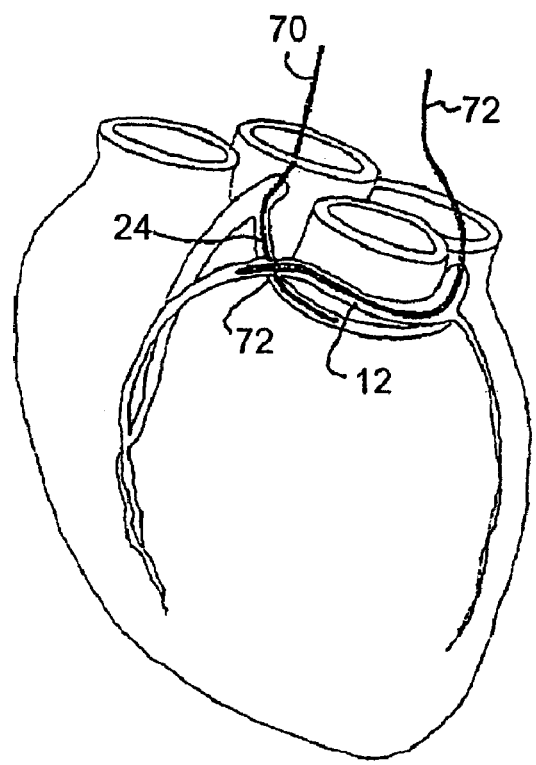
FIG. 7 is a schematic drawing showing a method of determining the crossover point between a circumflex artery and a coronary sinus.

An alternative method of determining the relative positions of the vessels is shown in FIG. 7. In this method, guide wires 70 and 72 are inserted into the coronary sinus 12 and into the circumflex artery 24 or other coronary artery, and the relative positions of the guide wires are viewed on a fluoroscope to identify the crossover point 74.

Figure 8:
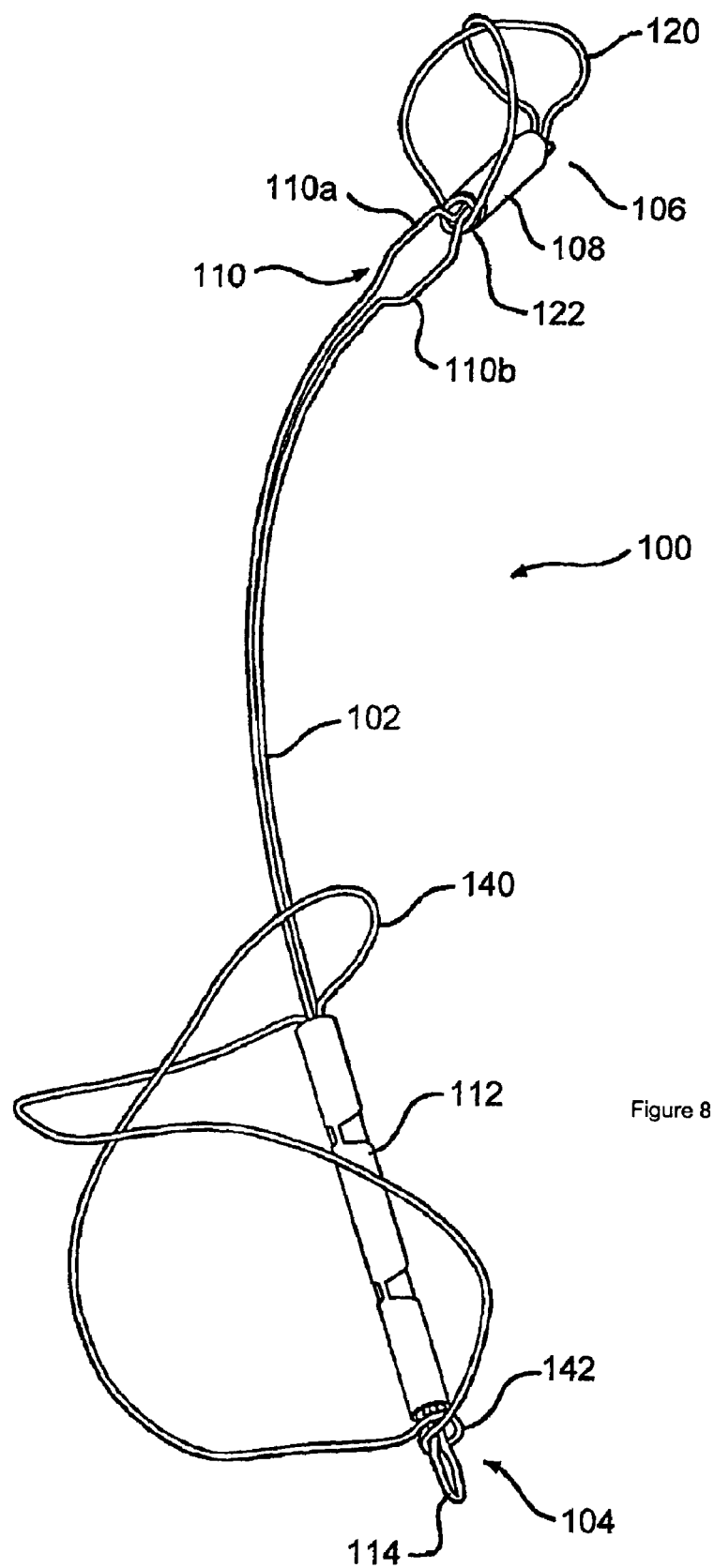
FIG. 8 is a perspective drawing of a tissue shaping device according to one embodiment of this invention.

FIG. 8 illustrates one embodiment of a tissue shaping device in accordance with the present invention. The tissue shaping device 100 includes a connector or support wire 102 having a proximal end 104 and a distal end 106. The support wire 102 is made of a biocompatible material such as stainless steel or a shape memory material such as nitinol wire.

In one embodiment of the invention, connector 102 comprises a double length of nitinol wire that has both ends positioned within a distal crimp tube 108. Proximal to the proximal end of the crimp tube 108 is a distal lock bump 110 that is formed by the support wire bending away from the longitudinal axis of the support 102 and then being bent parallel to the longitudinal axis of the support before being bent again towards the longitudinal axis of the support to form one half 110a of distal lock bump 110. From distal lock bump 110, the wire continues proximally through a proximal crimp tube 112. On exiting the proximal end of the proximal crimp tube 112, the wire is bent to form an arrowhead-shaped proximal lock bump 114. The wire of the support 102 then returns distally through the proximal crimp tube 112 to a position just proximal to the proximal end of the distal crimp tube 108 wherein the wire is bent to form a second half 10b of the distal lock 110.

At the distal end of connector 102 is an actuatable distal anchor 120 that is formed of a flexible wire such as nitinol or some other shape memory material. As shown in FIG. 8, the wire forming the distal anchor has one end positioned within the distal crimp tube 108. After exiting the distal end of the crimp tube 108, the wire forms a figure eight configuration whereby it bends upward and radially outward from the longitudinal axis of the crimp tube 108. The wire then bends back proximally and crosses the longitudinal axis of the crimp tube 108 to form one leg of the figure eight. The wire is then bent to form a double loop eyelet or loop 122 around the longitudinal axis of the support wire 102 before extending radially outwards and distally back over the longitudinal axis of the crimp tube 108 to form the other leg of the figure eight. Finally, the wire is bent proximally into the distal end of the crimp tube 108 to complete the distal anchor 120.

The distal anchor is expanded by using a catheter or locking tool to exert an actuation force sliding eyelet 122 of the distal anchor from a position that is proximal to distal lock bump 110 on the connector to a position that is distal to distal lock bump 110. The bent-out portions 110a and 110b of connector 110 are spaced wider than the width of eyelet 122 and provide camming surfaces for the locking action. Distal movement of eyelet 122 pushes these camming surfaces inward to permit eyelet 122 to pass distally of the lock bump 110, then return to their original spacing to keep eyelet 122 in the locked position.

Actuatable proximal anchor 140 is formed and actuated in a similar manner by moving eyelet 142 over lock bump 114. Both the distal and the proximal anchor provide anchoring forces of at least one pound, and most preferably two pounds.

Figure 9:
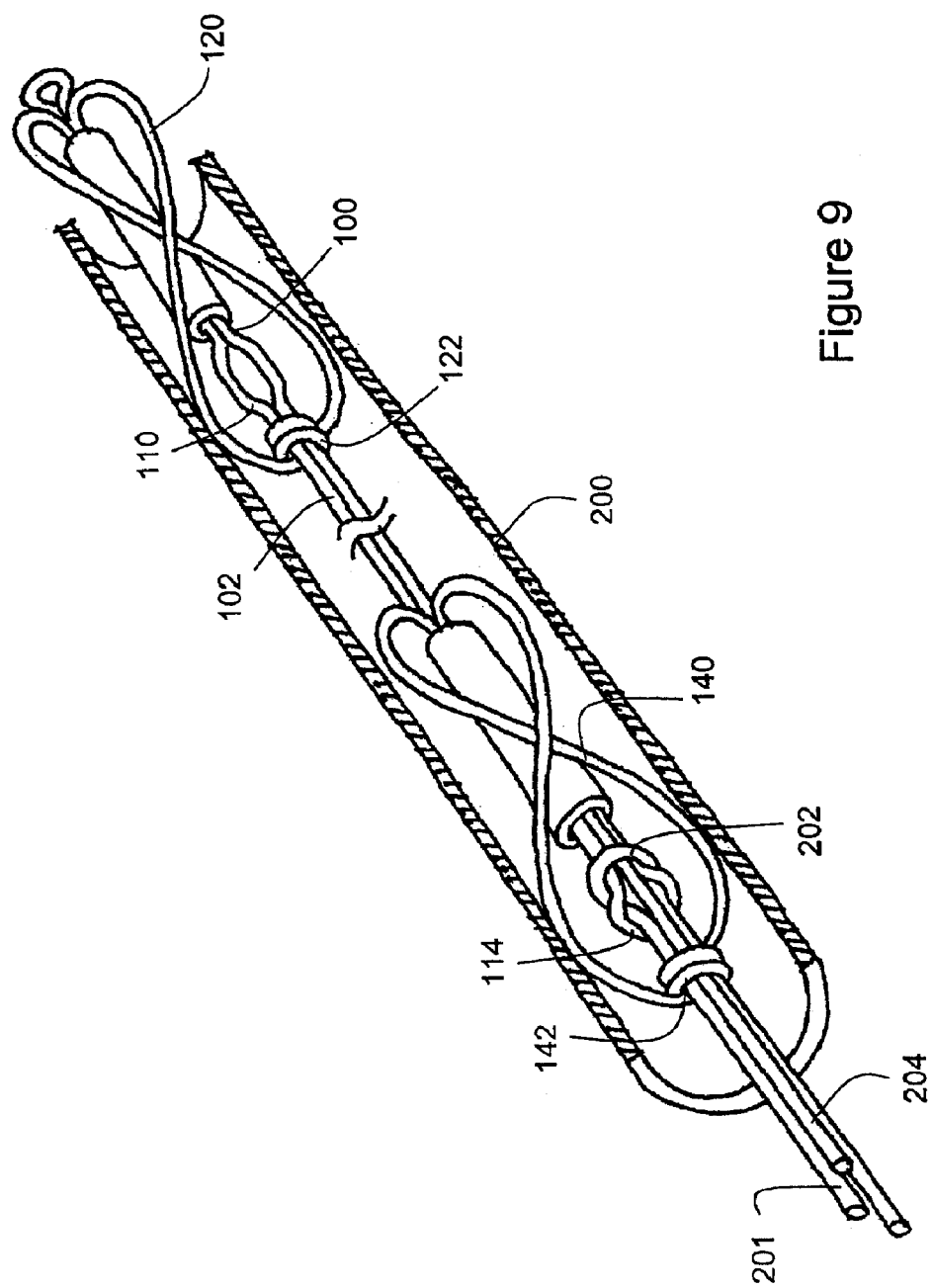
FIG. 9 is a partial sectional view of the tissue shaping device of FIG. 8 in an unexpanded configuration within a catheter.

FIG. 9 illustrates one method for delivering a tissue shaping device 100 in accordance with the present invention to a desired location in the body, such as the coronary sinus to treat mitral valve regurgitation. As indicated above, device 100 is preferably loaded into and routed to a desired location within a catheter 200 with the proximal and distal anchors in an unexpanded or deformed condition. That is, eyelet 122 of distal anchor 120 is positioned proximal to the distal lock bump 110 and the eyelet 142 of the proximal anchor 140 is positioned proximal to the proximal lock bump 114. The physician ejects the distal end of the device from the catheter 200 into the coronary sinus by advancing the device or retracting the catheter or a combination thereof. A pusher (not shown) provides distal movement of the device with respect to catheter 200, and a tether 201 provides proximal movement of the device with respect to catheter 200.

Because of the inherent elasticity of the material from which it is formed, the distal anchor begins to expand as soon as it is outside the catheter. Once the device is properly positioned, catheter 200 is advanced to place an actuation force on distal anchor eyelet 122 to push it distally over the distal lock bump 110 so that the distal anchor 120 further expands and locks in place to securely engage the wall of the coronary sinus. Next, a proximally-directed force is applied to connector 102 and distal anchor 120 via a tether or control wire 201 extending through catheter outside the patient to apply sufficient pressure on the tissue adjacent the connector to modify the shape of that tissue. In the case of the mitral valve, fluoroscopy, ultrasound or other imaging technology may be used to see when the device supplies sufficient pressure on the mitral valve to aid in its complete closure with each ventricular contraction without otherwise adversely affecting the patient.

The proximally directed reshaping force causes the proximal anchor 140 to move proximally. In one embodiment, for example, proximal anchor 140 can be moved about 1-6 cm., most preferably at least 2 cm., proximally to reshape the mitral valve tissue. The proximal anchor 140 is then deployed from the catheter and allowed to begin its expansion. The locking tool applies an actuation force on proximal anchor eyelet 142 to advance it distally over the proximal lock bump 114 to expand and lock the proximal anchor, thereby securely engaging the coronary sinus wall to maintain the proximal anchor's position and to maintain the reshaping pressure of the connector against the coronary sinus wall. Alternatively, catheter 200 may be advanced to lock proximal anchor 140.

Finally, the mechanism for securing the proximal end of the device can be released. In one embodiment, the securement is made with a braided loop 202 at the end of tether 201 and a lock wire 204. The lock wire 204 is withdrawn thereby releasing the loop 202 so it can be pulled through the proximal lock bump 114 at the proximal end of device 100.

Reduction in mitral valve regurgitation using devices of this invention can be maximized by deploying the distal anchor as far distally in the coronary sinus as possible. In some instances it may be desirable to implant a shorter tissue shaping device, such as situations where the patient's circumflex artery crosses the coronary sinus relatively closer to the ostium or situations in which the coronary sinus itself is shorter than normal. As can be seen from FIG. 9, anchor 120 in its unexpanded configuration extends proximally along connector 102 within catheter 200. Making the device shorter by simply shortening the connector, however, may cause the eyelet 122 and proximal portion of the distal anchor 120 to overlap with portions of the proximal anchor when the device is loaded into a catheter, thereby requiring the catheter diameter to be larger than is needed for longer versions of the device. For mitral valve regurgitation applications, a preferred catheter diameter is ten french or less (most preferably nine french), and the tissue shaping device in its unexpanded configuration must fit within the catheter.

FIGS. 10-23 show embodiments of the device of this invention having flexible and expandable wire anchors which permit the delivery of tissue shaping devices 60 mm or less in length by a ten french (or less) catheter. In some embodiments, one or both of the anchors are provided with bending points about which the anchors deform when placed in their unexpanded configuration for delivery by a catheter or recapture into a catheter. These bending points enable the anchors to deform into configurations that minimize overlap with other elements of the device. In other embodiments, the distal anchor is self-expanding, thereby avoiding the need for a proximally-extending eyelet in the anchor's unexpanded configuration that might overlap with the unexpanded proximal anchor within the delivery and/or recapture catheter.

Figure 10:
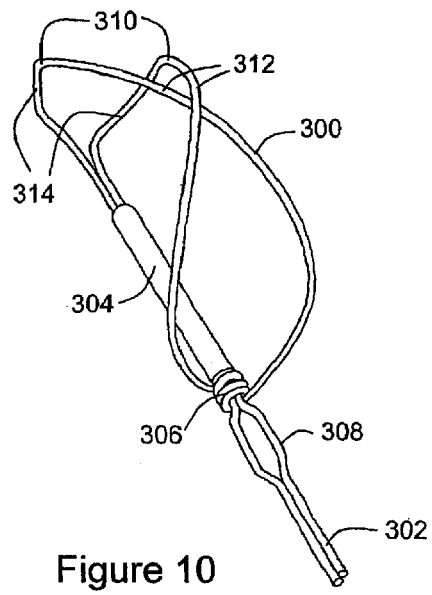
FIG. 10 is a perspective view of an anchor for use with a tissue shaping device according to this invention.

FIG. 10 shows an actuatable anchor design suitable for a shorter tissue shaping device similar to the device shown in FIGS. 8 and 9. In this embodiment, distal anchor 300 is disposed distal to a connector 302. As in the embodiment of FIG. 8, anchor 300 is formed in a figure eight configuration from flexible wire such as nitinol held by a crimp tube 304. An eyelet 306 is formed around the longitudinal axis of connector 302. A distally directed actuation force on eyelet 306 moves it over a lock bump 308 formed in connector 302 to actuate and lock anchor 300.

FIG. 10 shows anchor 300 in an expanded configuration. In an unexpanded configuration, such as a configuration suitable for loading anchor 300 and the rest of the tissue shaping device into a catheter for initial deployment to treat mitral valve regurgitation, eyelet 306 is disposed proximal to lock bump 308, and the figure eight loops of anchor 300 are compressed against crimp 304. In order to limit the proximal distance eyelet 306 must be moved along the connector to compress anchor 300 into an unexpanded configuration, bending points 310 are formed in the distal struts of anchor 300. Bending points 310 are essentially kinks, i.e., points of increased curvature, formed in the wire. When anchor 300 is compressed into an unexpanded configuration, bending points 310 deform such that the upper arms 312 of the distal struts bend around bending points 310 and move toward the lower arms 314 of the distal struts, thereby limiting the distance eyelet 306 and the anchor's proximal struts must be moved proximally along the connector to compress the anchor.

Likewise, if distal anchor were to be recaptured into a catheter for redeployment or removal from the patient, anchor 300 would deform about bending points 310 to limit the cross-sectional profile of the anchor within the catheter, even if eyelet 306 were not moved proximally over lock bump 308 during the recapture procedure. Bending points may also be provided on the proximal anchor in a similar fashion.

As stated above, distal anchor 300 may be part of a tissue shaping device (such as that shown in FIGS. 8 and 9) having a proximal anchor and a connector disposed between the anchors. To treat mitral valve regurgitation, distal anchor 300 may be deployed from a catheter and expanded with an actuation force to anchor against the coronary sinus wall to provide an anchoring force of at least one pound, preferably at least two pounds, and to lock anchor 300 in an expanded configuration. A proximally directed force is applied to distal anchor 300 through connector 302, such as by moving the proximal anchor proximally about 1-6 cm., more preferably at least 2 cm., by pulling on a tether or control wire operated from outside the patient. The proximal anchor may then be deployed to maintain the reshaping force of the device.

One aspect of anchor 300 is its ability to conform and adapt to a variety of vessel sizes. For example, when anchor 300 is expanded inside a vessel such as the coronary sinus, the anchor's wire arms may contact the coronary sinus wall before the eyelet 306 has been advanced distally over lock bump 308 to lock the anchor in place. While continued distal advancement of eyelet 306 will create some outward force on the coronary sinus wall, much of the energy put into the anchor by the anchor actuation force will be absorbed by the deformation of the distal struts about bending points 310, which serve as expansion energy absorption elements and thereby limit the radially outward force on the coronary sinus wall. This feature enables the anchor to be used in a wider range of vessel sizes while reducing the risk of over-expanding the vessel.

Figure 11:
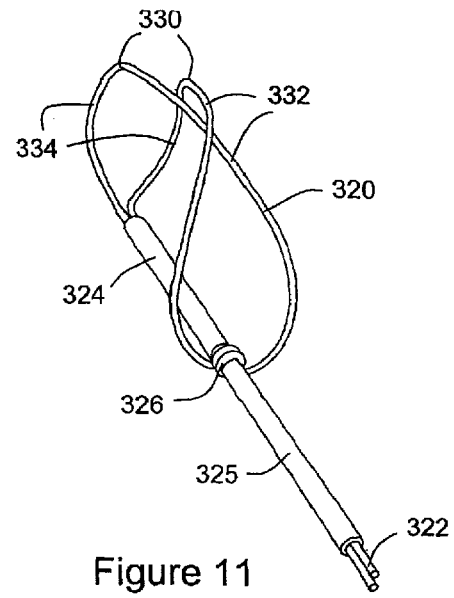
FIG. 11 is a perspective view of another anchor for use with a tissue shaping device according to this invention.

FIG. 11 shows another anchor design suitable for a shorter tissue shaping device similar to the device shown in FIGS. 8 and 9. In this embodiment, distal anchor 320 is disposed distal to a connector 322. As in the embodiment of FIG. 8, anchor 320 is formed in a figure eight configuration from flexible wire such as nitinol held by a crimp tube 324. Unlike the embodiment of FIG. 10, however, anchor 320 is self-expanding and is not actuatable. Eyelet 326 is held in place by a second crimp 325 to limit or eliminate movement of the anchor's proximal connection point proximally or distally, e.g., along connector 322.

FIG. 11 shows anchor 320 in an expanded configuration. In an unexpanded configuration, such as a configuration suitable for loading anchor 320 and the rest of the tissue shaping device into a catheter for initial deployment to treat mitral valve regurgitation, the figure eight loops of anchor 320 are compressed. Bending points 330 are formed in the distal struts of anchor 320. When anchor 320 is compressed into an unexpanded configuration, bending points 330 deform such that the upper arms 332 of the distal struts bend around bending points 330 and move toward the lower arms 334 of the distal struts. Depending upon the exact location of bending points 330, very little or none of the wire portion of anchor 320 is disposed proximally along crimp 325 or connector 322 when anchor 320 is in its unexpanded configuration.

Likewise, if distal anchor were to be recaptured into a catheter for redeployment or removal from the patient, anchor 320 would deform about bending points 330 to limit the cross-sectional profile of the anchor within the catheter. Bending points may also be provided on the proximal anchor in a similar fashion.

Distal anchor 320 may be part of a tissue shaping device (such as that shown in FIGS. 8 and 9) having a proximal anchor and a connector disposed between the anchors. Due to the superelastic properties of its shape memory material, distal anchor 320 may be deployed from a catheter to self-expand to anchor against the coronary sinus wall to provide an anchoring force of at least one pound, preferably at least two pounds. A proximally directed force may then be applied to distal anchor 320 through connector 322, such as by moving the proximal anchor proximally about 1-6 cm., more preferably at least 2 cm., by pulling on a tether or control wire operated from outside the patient. The proximal anchor may then be deployed to maintain the reshaping force of the device.

Figure 12:
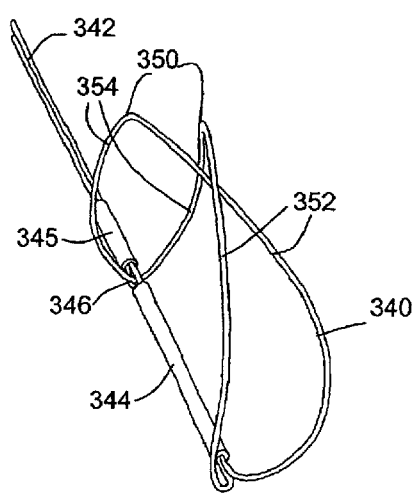
FIG. 12 is a perspective view of yet another anchor for use with a tissue shaping device according to this invention.

FIG. 12 shows another embodiment of an anchor suitable for use in a shorter tissue shaping device. In this embodiment, distal anchor 340 is disposed distal to a connector 342. As in the embodiment of FIG. 11, anchor 340 is formed in a figure eight configuration from flexible wire such as nitinol held by a crimp tube 344. Also like that embodiment, anchor 340 is self-expanding and is not actuatable. The loop of anchor 340 forming the anchor's proximal struts passes through a loop 346 extending distally from a second crimp 345 to limit or eliminate movement of the anchor's proximal struts proximally or distally, e.g., along connector 342.

FIG. 12 shows anchor 340 in an expanded configuration. Like the device of FIG. 11, in an unexpanded configuration, such as a configuration suitable for loading anchor 340 and the rest of the tissue shaping device into a catheter for initial deployment to treat mitral valve regurgitation, the figure eight loops of anchor 340 are compressed. Unlike the FIG. 11 embodiment, however, bending points 350 are formed in the proximal struts of anchor 340. When anchor 340 is compressed into an unexpanded configuration, bending points 350 deform such that the upper arms 352 of the distal struts bend around bending points 350 and move toward the lower arms 354 of the distal struts. The amount of the wire portion of anchor 340 extending proximally along crimp 345 and connector 342 in its unexpanded configuration depends on the location of bending points 350. In one embodiment, the bending points are formed at the tallest and widest part of the proximal struts.

Distal anchor 340 may be part of a tissue shaping device (such as that shown in FIGS. 8 and 9) having a proximal anchor and a connector disposed between the anchors. Due to the superelastic properties of its shape memory material, distal anchor 340 may be deployed from a catheter to self-expand to anchor against the coronary sinus wall to provide an anchoring force of at least one pound, preferably at least two pounds. A proximally directed force may then be applied to distal anchor 340 through connector 342, such as by moving the proximal anchor proximally about 1-6 cm., more preferably at least 2 cm., by pulling on a tether or control wire operated from outside the patient. The proximal anchor may then be deployed to maintain the reshaping force of the device.

Bending points 350 also add to the anchoring force of distal anchor 340, e.g., by causing the anchor height to increase as the proximal struts become more perpendicular to the connector in response to a proximally directed force, thereby increasing the anchoring force. In the same manner, bending points may be added to the distal struts of a proximal anchor to increase the proximal anchor's anchoring force in response to a distally directed force.

Figure 13:
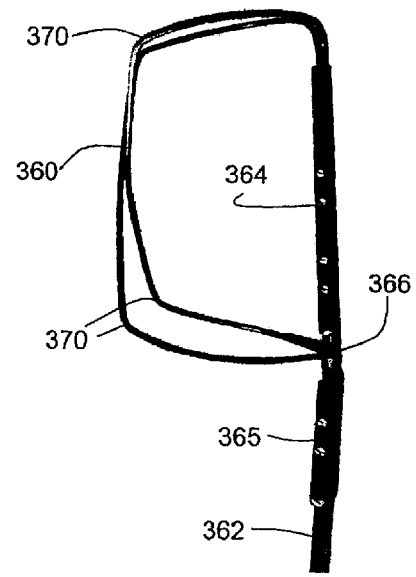
FIG. 13 is a perspective view of still another anchor for use with a tissue shaping device according to this invention.

FIG. 13 shows yet another embodiment of an anchor suitable for use in a shorter tissue shaping device. In this embodiment, distal anchor 360 is disposed distal to a connector 362. As in the embodiment of FIG. 12, anchor 360 is formed in a figure eight configuration from flexible wire such as nitinol held by a crimp tube 364. Also like that embodiment, anchor 360 is self-expanding and is not actuatable. The loop of anchor 360 forming the anchor's proximal struts passes through a loop 366 extending distally from a second crimp 365 to limit or eliminate movement of the anchor's proximal struts proximally or distally, e.g., along connector 362.

FIG. 13 shows anchor 360 in an expanded configuration. Like the device of FIG. 12, in an unexpanded configuration, such as a configuration suitable for loading anchor 360 and the rest of the tissue shaping device into a catheter for initial deployment to treat mitral valve regurgitation, the figure eight loops of anchor 360 are compressed. Unlike the FIG. 12 embodiment, however, bending points 370 are formed in both the proximal struts and the distal struts of anchor 360.

Anchor 360 may be used as part of a tissue shaping device like the embodiments discussed above.

Figure 14:
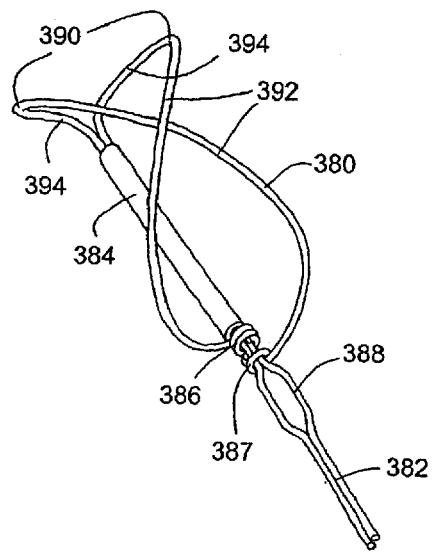
FIG. 14 is a perspective view of another anchor for use with a tissue shaping device according to this invention.

FIG. 14 shows an actuatable anchor design suitable for a shorter tissue shaping device similar to the device shown in FIGS. 8 and 9. In this embodiment, distal anchor 380 is disposed distal to a connector 382. As in the other embodiments, anchor 380 is formed in a figure eight configuration from flexible wire such as nitinol held by a crimp tube 384. In contrast to the embodiment of FIG. 10, eyelets 386 and 387 are formed in each of the anchor's proximal struts around the longitudinal axis of connector 382. This arrangement reduces the radially outward force of the anchor. A distally directed actuation force on eyelets 386 and 387 move them over a lock bump 388 formed in connector 382 to actuate and lock anchor 380.

FIG. 14 shows anchor 380 in an expanded configuration. In an unexpanded configuration, such as a configuration suitable for loading anchor 380 and the rest of the tissue shaping device into a catheter for initial deployment to treat mitral valve regurgitation, eyelets 386 and 387 are disposed proximal to lock bump 388 and the figure eight loops of anchor 380 are compressed against crimp 384. In order to limit the proximal distance eyelets 386 and 387 must be moved to compress anchor 380 into an unexpanded configuration, bending points 390 are formed in the distal struts of anchor 380. When anchor 380 is compressed into an unexpanded configuration, bending points 390 deform such that the upper arms 392 of the distal struts bend around bending points 390 and move toward the lower arms 394 of the distal struts, thereby limiting the distance eyelets 386 and 387 and the anchor's proximal struts must be moved proximally along the connector to compress the anchor.

If distal anchor were to be recaptured into a catheter for redeployment or removal from the patient, anchor 380 would deform about bending points 390 to limit the cross-sectional profile of the anchor within the catheter, even if eyelets 386 and 387 were not moved proximally over lock bump 388 during the recapture procedure. Bending points may also be provided on the proximal anchor in a similar fashion.

As with the other embodiments above, distal anchor 380 may be part of a tissue shaping device (such as that shown in FIGS. 8 and 9) having a proximal anchor and a connector disposed between the anchors. To treat mitral valve regurgitation, distal anchor 380 may be deployed from a catheter and expanded with an actuation force to anchor against the coronary sinus wall to provide an anchoring force of at least one pound, preferably at least two pounds, and to lock anchor 380 in an expanded configuration. A proximally directed force is applied to distal anchor 380 through connector 382, such as by moving the proximal anchor proximally about 1-6 cm., more preferably at least 2 cm., by pulling on a tether or control wire operated from outside the patient. The proximal anchor may then be deployed to maintain the reshaping force of the device.

As with other embodiments, one aspect of anchor 380 is its ability to conform and adapt to a variety of vessel sizes. For example, when anchor 380 is expanded inside a vessel such as the coronary sinus, the anchor's wire arms may contact the coronary sinus wall before the eyelets 386 and 387 have been advance distally over lock bump 388 to lock the anchor in place. While continued distal advancement of eyelet 386 will create some outward force on the coronary sinus wall, much of the energy put into the anchor by the anchor actuation force will be absorbed by the deformation of the distal struts about bending points 390.

Figure 15:
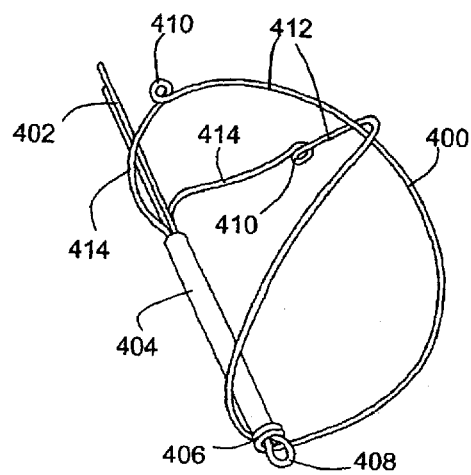
FIG. 15 is a perspective view of yet another anchor for use with a tissue shaping device according to this invention.

FIG. 15 shows yet another embodiment of an actuatable anchor for use in a shorter tissue shaping device. Proximal anchor 400 is disposed proximal to a connector 402. As in other embodiments, anchor 400 is formed in a figure eight configuration from flexible wire such as nitinol held by a crimp tube 404. An eyelet 406 is formed around a lock bump 408 extending proximally from crimp 404. A distally directed actuation force on eyelet 406 moves it over lock bump 408 to actuate and lock anchor 400.

FIG. 15 shows anchor 400 in an expanded configuration. When anchor 400 is compressed into an unexpanded configuration, bending points 410 formed as loops in the anchor wire deform such that the upper arms 412 of the distal struts bend around bending points 410 and move toward the lower arms 414 of the distal struts. As with the other embodiments, proximal anchor 400 may be part of a tissue shaping device (such as that shown in FIGS. 8 and 9) having a distal anchor and a connector disposed between the anchors.

Like other embodiments, one aspect of anchor 400 is its ability to conform and adapt to a variety of vessel sizes. For example, when anchor 400 is expanded inside a vessel such as the coronary sinus, the anchor's wire arms may contact the coronary sinus wall before the eyelet 406 has been advanced distally over lock bump 408 to lock the anchor in place. While continued distal advancement of eyelet 406 will create some outward force on the coronary sinus wall, much of the energy put into the anchor by the anchor actuation force will be absorbed by the deformation of the distal struts about bending points 410, which serve as expansion energy absorption elements and thereby limit the radially outward force on the coronary sinus wall.

Figure 16:
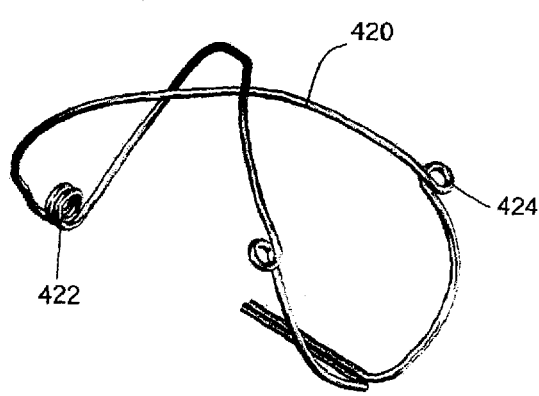
FIG. 16 is a perspective view of part of an anchor for use with a tissue shaping device according to this invention.

In other embodiments, the looped bending points of the FIG. 15 embodiment may be formed on the anchor's proximal struts in addition to or instead of on the distal struts. The looped bending point embodiment may also be used in a distal anchor, as shown in FIG. 16 (without the crimp or connector). Note that in the embodiment of FIG. 16 the proximal and distal struts of anchor 420 as well as the eyelet 422 and bending points 424 are formed from a single wire.

Figure 17:
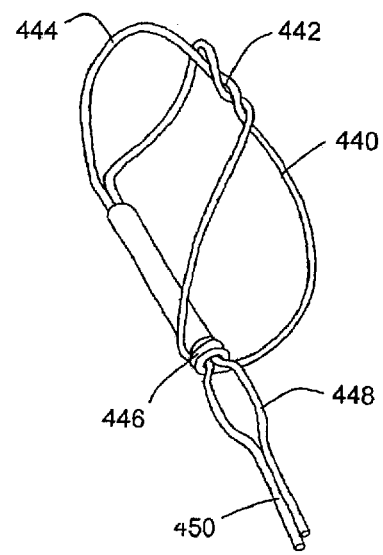
FIG. 17 is a perspective view of still another anchor for use with a tissue shaping device according to this invention.

FIG. 17 shows an embodiment of a distal anchor 440 similar to that of FIG. 10 suitable for use in a shorter tissue shaping device. In this embodiment, however, extra twists 442 are added at the apex of the anchor's figure eight pattern. As in the FIG. 10 embodiment, bending points 444 are formed in the anchor's distal struts. As shown, anchor 440 is actuatable by moving eyelet 446 distally over a lock bump 448 formed in connector 450. Anchor 440 may also be made as a self-expanding anchor by limiting or eliminating movement of the proximal struts of anchor 440 along connector 450, as in the embodiment shown in FIG. 11. As with other embodiments, the bending points help anchor 440 adapt and conform to different vessel sizes. In addition, the extra twists 442 also help the anchor adapt to different vessel diameters by keeping the anchor's apex together.

As in the other embodiments, anchor 440 is preferably formed from nitinol wire. Anchor 440 may be used as part of a tissue shaping device in a manner similar to the anchor of FIG. 10 (for the actuatable anchor embodiment) or the anchor of FIG. 11 (for the self-expanding anchor embodiment). Anchor 440 may also be used as a proximal anchor.

Figure 18:
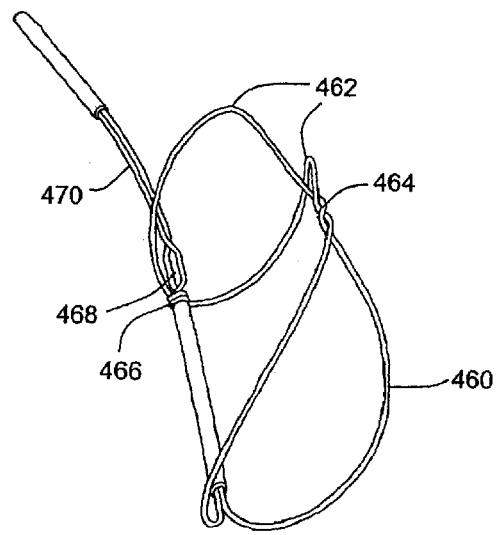
FIG. 18 is a perspective view of another anchor for use with a tissue shaping device according to this invention.

FIG. 18 shows an embodiment of a distal anchor 460 similar to that of FIG. 17. In this embodiment, however, the bending points 462 are formed in the anchor's proximal struts, as in the self-expanding anchor shown in FIG. 12. As in the FIG. 17 embodiment, extra twists 464 are added at the apex of the anchor's figure eight pattern. As shown, anchor 460 is actuatable by moving eyelet 466 distally over a lock bump 468 formed in connector 470. Anchor 460 may also be made as a self-expanding anchor by limiting or eliminating movement of the proximal connection point of anchor 460 along connector 470, as in the embodiment shown in FIG. 11. As with the embodiment of FIG. 17, the bending points help anchor 460 adapt and conform to different vessel sizes. In addition, the extra twists 464 also help the anchor adapt to different vessel diameters by keeping the anchor's apex together.

As in the other embodiments, anchor 460 is preferably formed from nitinol wire. Anchor 460 may be used as part of a tissue shaping device in a manner similar to the anchor of FIG. 10 (for the actuatable anchor embodiment) or the anchor of FIG. 11 (for the self-expanding anchor embodiment). Anchor 460 may also be used as a proximal anchor.

Figure 19:
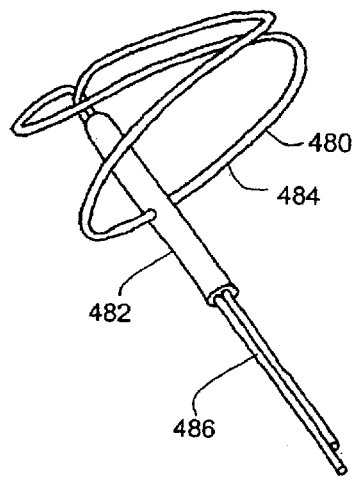
FIG. 19 is a perspective view of yet another anchor for use with a tissue shaping device according to this invention.

FIG. 19 shows an embodiment of a self-expanding distal anchor 480 suitable for use in a shorter tissue shaping device. As in the other embodiments, anchor 480 is formed in a figure eight configuration from flexible wire such as nitinol held by a crimp tube 482. The base of the figure eight pattern is narrower in this embodiment, however, with the anchor's proximal struts 484 passing through crimp 482.

Distal anchor 480 may be part of a tissue shaping device (such as that shown in FIGS. 8 and 9) having a proximal anchor and a connector disposed between the anchors. To treat mitral valve regurgitation, distal anchor 480 may be deployed from a catheter and allowed to self-expand to anchor against the coronary sinus wall to provide an anchoring force of at least one pound, preferably at least two pounds. A proximally directed force is applied to distal anchor 480 through connector 486, such as by moving the proximal anchor proximally about 1-6 cm., more preferably at least 2 cm., by pulling on a tether or control wire operated from outside the patient. The proximal anchor may then be deployed to maintain the reshaping force of the device.

Figure 20:
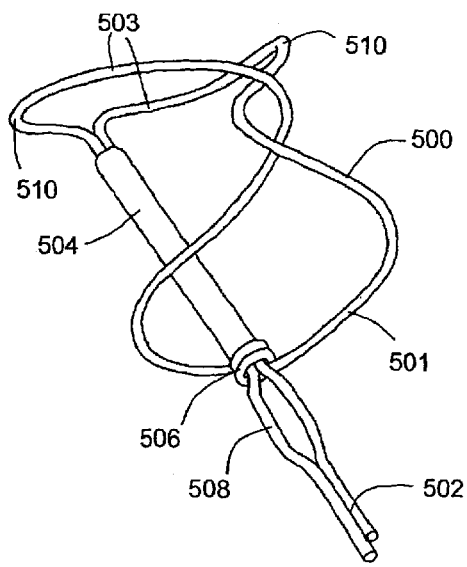
FIG. 20 is a perspective view of still another anchor for use with a tissue shaping device according to this invention.

FIG. 20 shows an embodiment of a distal anchor suitable for use in a shorter tissue shaping device and similar to that of FIG. 10. In this embodiment, distal anchor 500 is disposed distal to a connector 502. As in other embodiments, anchor 500 is formed in a figure eight configuration from flexible wire such as nitinol held by a crimp tube 504. An eyelet 506 is formed around the longitudinal axis of connector 502. A distally directed actuation force on eyelet 506 moves it over a lock bump 508 formed in connector 502 to actuate and lock anchor 500.

The angle of proximal struts 501 and the angle of distal struts 503 are wider than corresponding angles in the FIG. 10 embodiment, however, causing anchor 500 to distend more in width than in height when expanded, as shown. In an unexpanded configuration, such as a configuration suitable for loading anchor 500 and the rest of the tissue shaping device into a catheter for initial deployment to treat mitral valve regurgitation, eyelet 506 is disposed proximal to lock bump 508 and the figure eight loops of anchor 500 are compressed against crimp 504. In order to limit the proximal distance eyelet 506 must be moved along the connector to compress anchor 500 into an unexpanded configuration, bending points 510 are formed in the distal struts 503, as in the FIG. 10 embodiment, to limit the width of the device in its unexpanded configuration within a catheter.

Distal anchor 500 may be part of a tissue shaping device (such as that shown in FIGS. 8 and 9) having a proximal anchor and a connector disposed between the anchors. To treat mitral valve regurgitation, distal anchor 500 may be deployed from a catheter and expanded with an actuation force to anchor against the coronary sinus wall to provide an anchoring force of at least one pound, preferably at least two pounds, and to lock anchor 500 in an expanded configuration. A proximally directed force is applied to distal anchor 500 through connector 502, such as by moving the proximal anchor proximally about 1-6 cm., more preferably at least 2 cm., by pulling on a tether or control wire operated from outside the patient. The proximal anchor may then be deployed to maintain the reshaping force of the device.

The anchor shown in FIG. 20 may be used as a proximal anchor. This anchor may also be formed as a self-expanding anchor.

Figure 21:
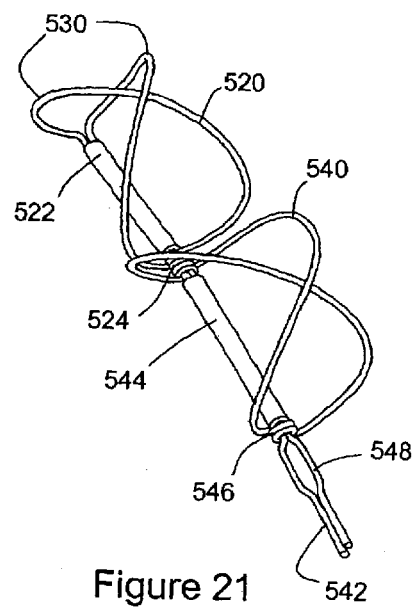
FIG. 21 is a perspective view of a tandem anchor for use with a tissue shaping device according to this invention.

FIG. 21 shows a tandem distal anchor according to another embodiment of this invention. Self-expanding anchor 520 is formed in a figure eight configuration from flexible wire such as nitinol held by a crimp tube 522. Eyelet 524 is held in place by the distal end of actuatable anchor 540 to limit or eliminate proximal and distal movement of the proximal struts of anchor 520. As in the anchor shown in FIG. 11, bending points 530 are formed in the distal struts of anchor 520. Depending upon the exact location of bending points 530, very little or none of the wire portion of anchor 520 is disposed proximal to the distal end of anchor 540 when anchor 520 is in its unexpanded configuration.

Likewise, if distal anchor were to be recaptured into a catheter for redeployment or removal from the patient, anchor 520 would deform about bending points 530 to limit the cross-sectional profile of the anchor within the catheter. Bending points may also be provided on the proximal anchor in a similar fashion.

Anchor 540 is similar to anchor 120 shown in FIG. 8. Anchor 540 is formed in a figure eight configuration from flexible wire such as nitinol held by a crimp tube 544. An eyelet 546 is formed around the longitudinal axis of connector 542. A distally directed actuation force on eyelet 546 moves it over a lock bump 548 formed in connector 542 to actuate and lock anchor 540.

Tandem anchors 520 and 540 may be part of a tissue shaping device (such as that shown in FIGS. 8 and 9) having a proximal anchor and a connector disposed between the anchors. Anchors 520 and 540 may be made from a single wire or from separate pieces of wire. To treat mitral valve regurgitation, distal anchors 520 and 540 may be deployed from a catheter. Self-expanding anchor 520 will then self-expand, and actuatable anchor 540 may be expanded and locked with an actuation force, to anchor both anchors against the coronary sinus wall to provide an anchoring force of at least one pound, preferably at least two pounds. A proximally directed force is applied to anchors 520 and 540 through connector 542, such as by moving the proximal anchor proximally about 1-6 cm., more preferably at least 2 cm., by pulling on a tether or control wire operated from outside the patient. The proximal anchor may then be deployed to maintain the reshaping force of the device.

While the anchor designs above were described as part of shorter tissue shaping devices, these anchors may be used in tissue shaping devices of any length.

Figure 22:
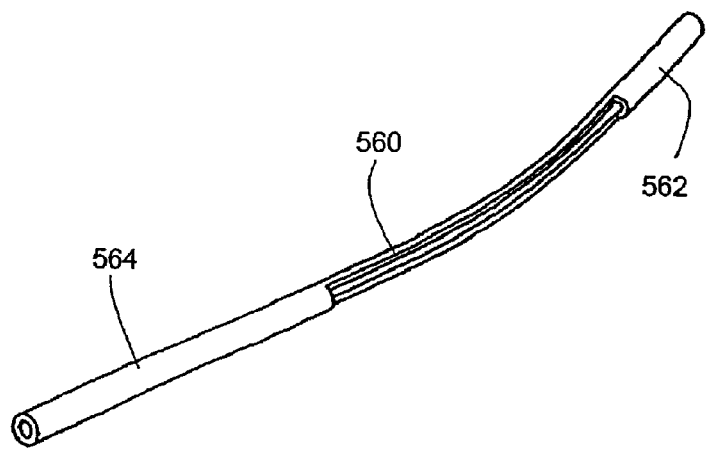
FIG. 22 is a perspective view of a connector with integral anchor crimps for us in a tissue shaping device according to this invention.
Figure 23:
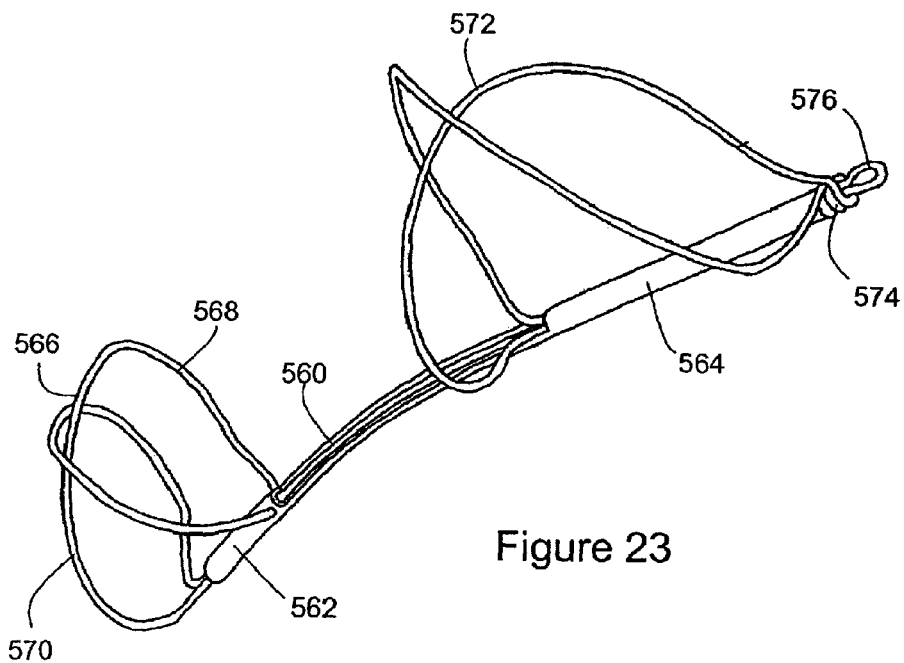
FIG. 23 is a perspective view of a tissue shaping device employing the connector of FIG. 22.

FIGS. 22 and 23 show an alternative embodiment in which the device's connector 560 is made integral with the distal and proximal crimp tubes 562 and 564. In this embodiment, connector 560 is formed by cutting away a section of a blank such as a nitinol (or other suitable material such as stainless steel) cylinder or tube, leaving crimp tube portions 562 and 564 intact. The radius of the semi-circular cross-section connector is therefore the same as the radii of the two anchor crimp tubes.

Other connector shapes are possible for an integral connector and crimp design, of course. For example, the device may be formed from a blank shaped as a flat ribbon or sheet by removing rectangular edge sections from a central section, creating an I-shaped sheet (e.g., nitinol or stainless steel) having greater widths at the ends and a narrower width in the center connector portion. The ends can then be rolled to form the crimp tubes, leaving the connector substantially flat. In addition, in alternative embodiments, the connector can be made integral with just one of the anchors.

As shown in FIG. 23, a distal anchor 566 is formed in a figure eight configuration from flexible wire such as nitinol. Distal anchor 566 is self-expanding, and its proximal struts 568 are held in place by crimp tube 562. Optional bending points may be formed in the proximal struts 568 or distal struts 570 of anchor 566.

A proximal anchor 572 is also formed in a figure eight configuration from flexible wire such as nitinol with an eyelet 574 on its proximal end. A distally directed actuation force on eyelet 574 moves it over a lock bump 576 extending proximally from crimp tube 564 to actuate and lock anchor 572. Lock bump 576 also serves as the connection point for a tether or control wire to deploy and actuate device in the manner described above with respect to FIGS. 8 and 9. Optional bending points may be formed in the proximal or distal struts of anchor 572.

Figure 24:
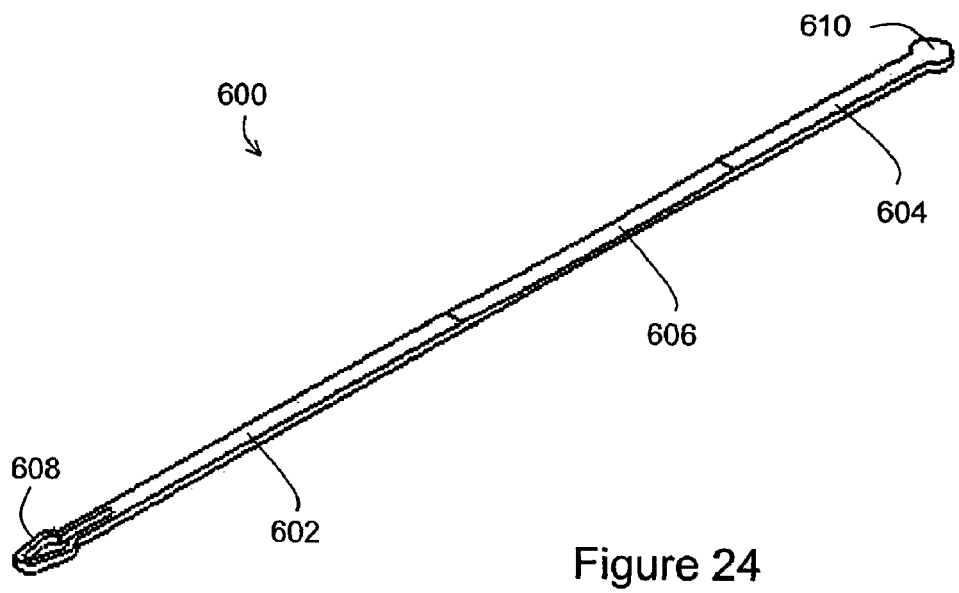
FIG. 24 is a perspective view of another connector for use with a tissue shaping device according to this invention.

When deployed in the coronary sinus to treat mitral valve regurgitation, the tissue shaping devices of this invention are subjected to cyclic bending and tensile loading as the patient's heart beats. FIG. 24 shows an alternative connector for use with the tissue shaping devices of this invention that distributes over more of the device any strain caused by the beat to beat bending and tensile loading.

Connector 600 has a proximal anchor area 602, a distal anchor area 604 and a central area 606. The distal anchor area may be longer than the distal anchor attached to it, and the proximal anchor area may be longer than the proximal anchor attached to it. An optional lock bump 608 may be formed at the proximal end of connector 600 for use with an actuatable proximal anchor and for connecting to a tether or control wire, as described above. An optional bulb 610 may be formed at the distal end of connector 600 to prevent accidental distal slippage of a distal anchor.

In order to reduce material fatigue caused by the heartbeat to heartbeat loading and unloading of the tissue shaping device, the moment of inertia of connector 600 varies along its length, particularly in the portion of connector disposed between the two anchors. In this embodiment, for example, connector 600 is formed as a ribbon or sheet and is preferably formed from nitinol having a rectangular cross-sectional area. The thickness of connector 600 is preferably constant in the proximal anchor area 602 and the distal anchor area 604 to facilitate attachment of crimps and other components of the anchors. The central area 606 has a decreasing thickness (and therefore a decreasing moment of inertia) from the border between central area 606 and proximal anchor area 602 to a point about at the center of central area 606, and an increasing thickness (and increasing moment of inertia) from that point to the border between central area 606 and distal anchor area 604. The varying thickness and varying cross-sectional shape of connector 600 change its moment of inertia along its length, thereby helping distribute over a wider area any strain from the heartbeat to heartbeat loading and unloading of the device and reducing the chance of fatigue failure of the connector material.

Figure 25:
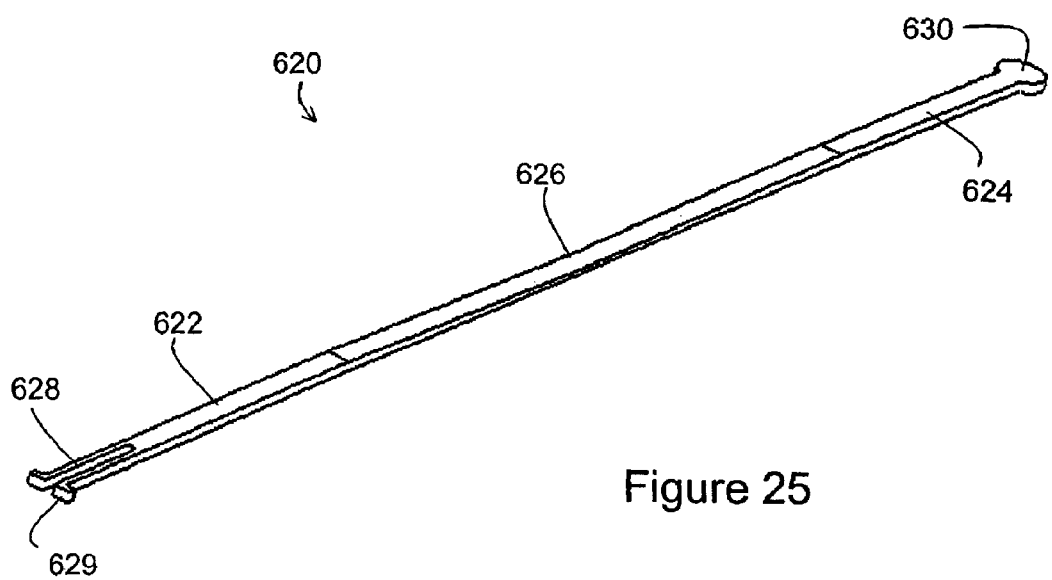
FIG. 25 is a perspective view of yet another connector for use with a tissue shaping device according to this invention.

FIG. 25 shows another embodiment of the connector. Like the previous embodiment, connector 620 has a proximal anchor area 622, a distal anchor area 624 and a central area 626. Proximal anchor area 622 has an optional two-tined prong 628 formed at its proximal end to facilitate attachment of a crimp and other anchor elements. Bent prong portions 629 may be formed at the proximal end of the prong to prevent accidental slippage of a proximal anchor. An optional bulb 630 may be formed at the distal end of connector 620 to prevent accidental distal slippage of a distal anchor.

Like the FIG. 24 embodiment, connector 620 is formed as a ribbon or sheet and is preferably formed from nitinol having a rectangular cross-sectional area. The thickness of connector 620 is preferably constant in the proximal anchor area 622 and the distal anchor area 624 to facilitate attachment of crimps and other components of the anchors. The central area 626 has a decreasing thickness (decreasing moment of inertia) from the border between central area 626 and proximal anchor area 622 to a point about at the center of central area 626, and an increasing thickness (increasing moment of inertia) from that point to the border between central area 626 and distal anchor area 624. The varying thickness and varying cross-sectional shape of connector 620 change its moment of inertia along its length, thereby helping distribute over a wider area any strain from the heartbeat to heartbeat loading and unloading of the device and reducing the chance of fatigue failure of the connector material.

Figure 26:
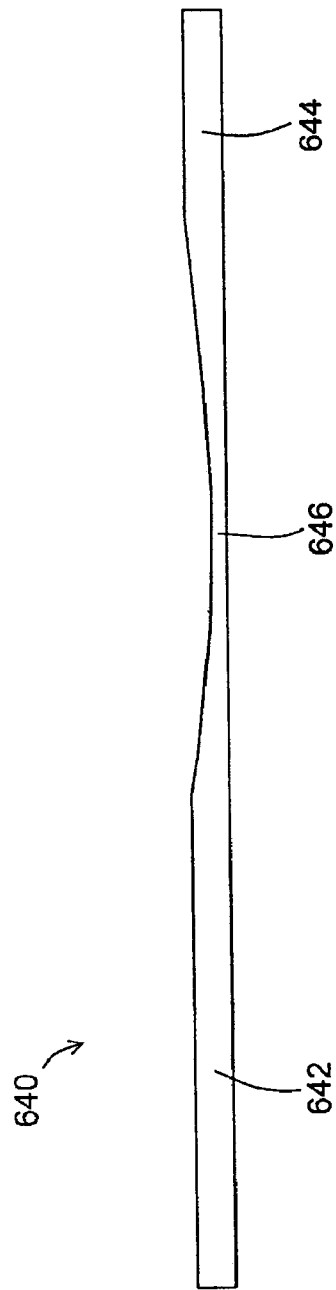
FIG. 26 is a side view of a connector for use with a tissue shaping device according to this invention.

FIG. 26 shows a connector 640 in profile. Connector 640 may be formed like the connectors 600 and 620 or FIGS. 24 and 25, respectively, or may have some other configuration.

Connector 640 has a proximal anchor area 642, a distal anchor area 644 and a central area 646. Connector 640 is preferably formed as a ribbon or sheet and is preferably formed from nitinol having a rectangular cross-sectional area.

In the embodiment shown in FIG. 26, the thicknesses of proximal anchor area 642 and distal anchor area 644 are constant. The thickness of central area 646 decreases from the border between central area 646 and proximal anchor area 642 to a point distal of that border and increases from a point proximal to the border between distal anchor area 644 and central area 646 to that border. The points in the central area where the thickness decrease ends and the thickness increase begins may be coincident or may be separated to form an area of uniform thickness within central area 646. In this embodiment, the thickness of the central area changes as a function of the square root of the distance from the borders between the central area and the proximal and distal anchor areas.

Figure 27:
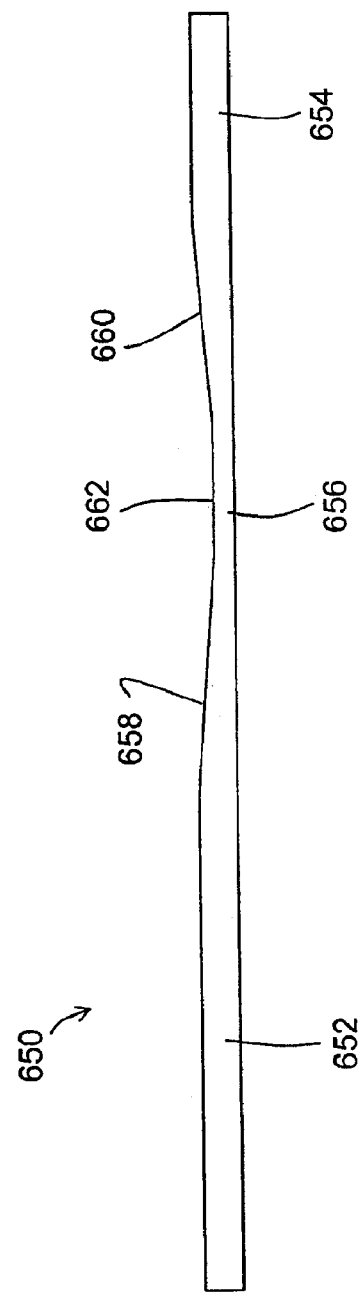
FIG. 27 is a side view of another connector for use with a tissue shaping device according to this invention.

FIG. 27 shows yet another embodiment of the connector. As in the embodiment of FIG. 26, connector 650 may be formed like the connectors 600 and 620 or FIGS. 24 and 25, respectively, or may have some other configuration. Connector 650 has a proximal anchor area 652, a distal anchor area 654 and a central area 656. Connector 650 is preferably formed as a ribbon or sheet and is preferably formed from nitinol having a rectangular cross-sectional area.

In the embodiment shown in FIG. 27, the thicknesses of proximal anchor area 652 and distal anchor area 654 are constant. The thickness of a proximal portion 658 of central area 656 decreases linearly from the border between central area 656 and proximal anchor area 652 to a constant thickness center portion 662 of central area 656, and the thickness of a distal portion 660 of central area 656 increases linearly from center portion 662 to the border between distal anchor area 654 and central area 656.

In other embodiments, the thickness of the connector may vary in other ways. In addition, the cross-sectional shape of the connector may be other than rectangular and may change over the length of the connector.

Figure 28:
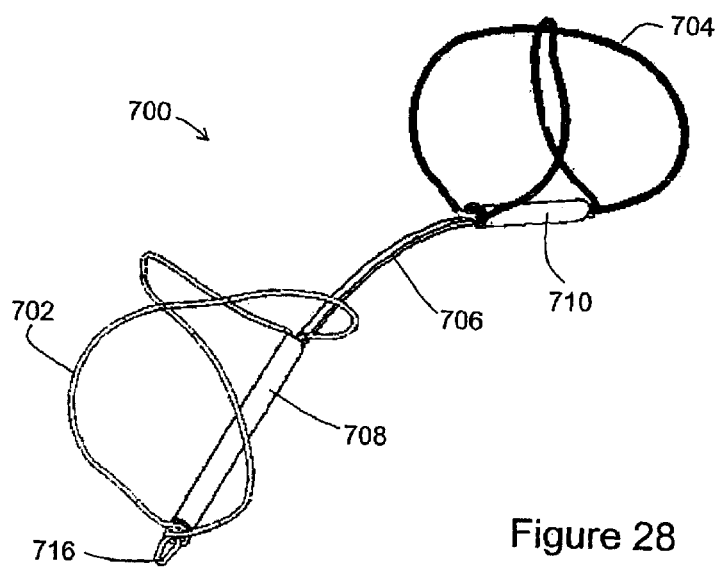
FIG. 28 is a perspective view of yet another tissue shaping device according to this invention.
Figure 29:
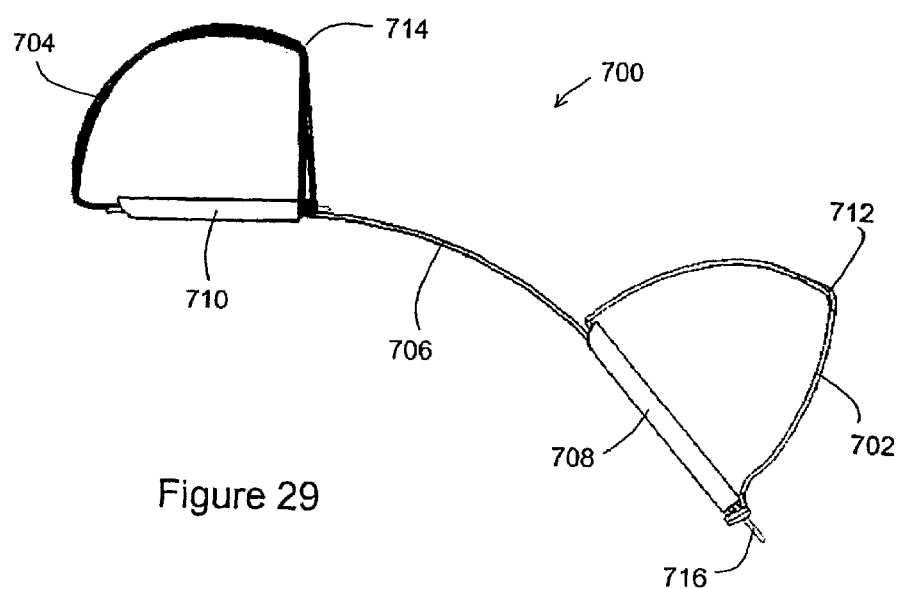
FIG. 29 is a side view of the tissue shaping device shown in FIG. 28.

FIGS. 28 and 29 show yet another embodiment of the invention. Tissue shaping device 700 has a connector 706 disposed between a proximal anchor 702 and a distal anchor 704. Connector 706 may be formed as a ribbon or sheet, such as the tapered connectors shown in FIGS. 24-27. Actuatable proximal anchor 702 is formed in a figure eight configuration from flexible wire such as nitinol and is fastened to connector 706 with a crimp tube 708. Likewise, self-expanding distal anchor 704 is formed in a figure eight configuration from flexible wire such as nitinol and is fastened to connector 706 with a crimp tube 710. A proximal lock bump 716 extends proximally from proximal anchor 702 for use in actuating and locking proximal anchor 702 and for connecting to a tether or control wire, as described above.

Bending points 712 are formed in the loops of proximal anchor 702, and bending points 714 are formed in the loops of distal anchor 704. When compressed into their unexpanded configurations for catheter-based delivery and deployment or for recapture into a catheter for redeployment or removal, the wire portions of anchors 702 and 704 bend about bending points 712 and 714, respectively, to limit the cross-sectional profile of the anchors within the catheter. The bending points also affect the anchor strength of the anchors and the adaptability of the anchors to different vessel diameters, as discussed above.

In addition to different coronary sinus lengths and varying distances from the ostium to the crossover point between the coronary sinus and the circumflex artery, the diameter of the coronary sinus at the distal and proximal anchor points can vary from patient to patient. The anchors described above may be made in a variety of heights and combined with connectors of varying lengths to accommodate this patient to patient variation. For example, tissue shaping devices deployed in the coronary sinus to treat mitral valve regurgitation can have distal anchor heights ranging from about 7 mm. to about 16 mm. and proximal anchor heights ranging from about 9 mm. to about 20 mm.

When treating a patient for mitral valve regurgitation, estimates can be made of the appropriate length for a tissue shaping device as well as appropriate anchor heights for the distal and proximal anchors. The clinician can then select a tissue shaping device having the appropriate length and anchor sizes from a set or sets of devices with different lengths and different anchor sizes, made, e.g., according to the embodiments described above. These device sets may be aggregated into sets or kits or may simply be a collection or inventory of different tissue shaping devices.

One way of estimating the appropriate length and anchor sizes of a tissue shaping device for mitral valve regurgitation is to view a fluoroscopic image of a coronary sinus into which a catheter with fluoroscopically viewable markings has been inserted. The crossover point between the coronary sinus and the circumflex artery can be determined as described above, and the screen size of the coronary sinus length proximal to that point and the coronary sinus diameter at the intended anchor locations can be measured. By also measuring the screen distance of the catheter markings and comparing them to the actual distance between the catheter marking, the length and diameter measures can be scaled to actual size. A tissue shaping device with the appropriate length and anchor sizes can be selected from a set or inventory of devices for deployment in the patient to treat mitral valve regurgitation.

Figure 30:
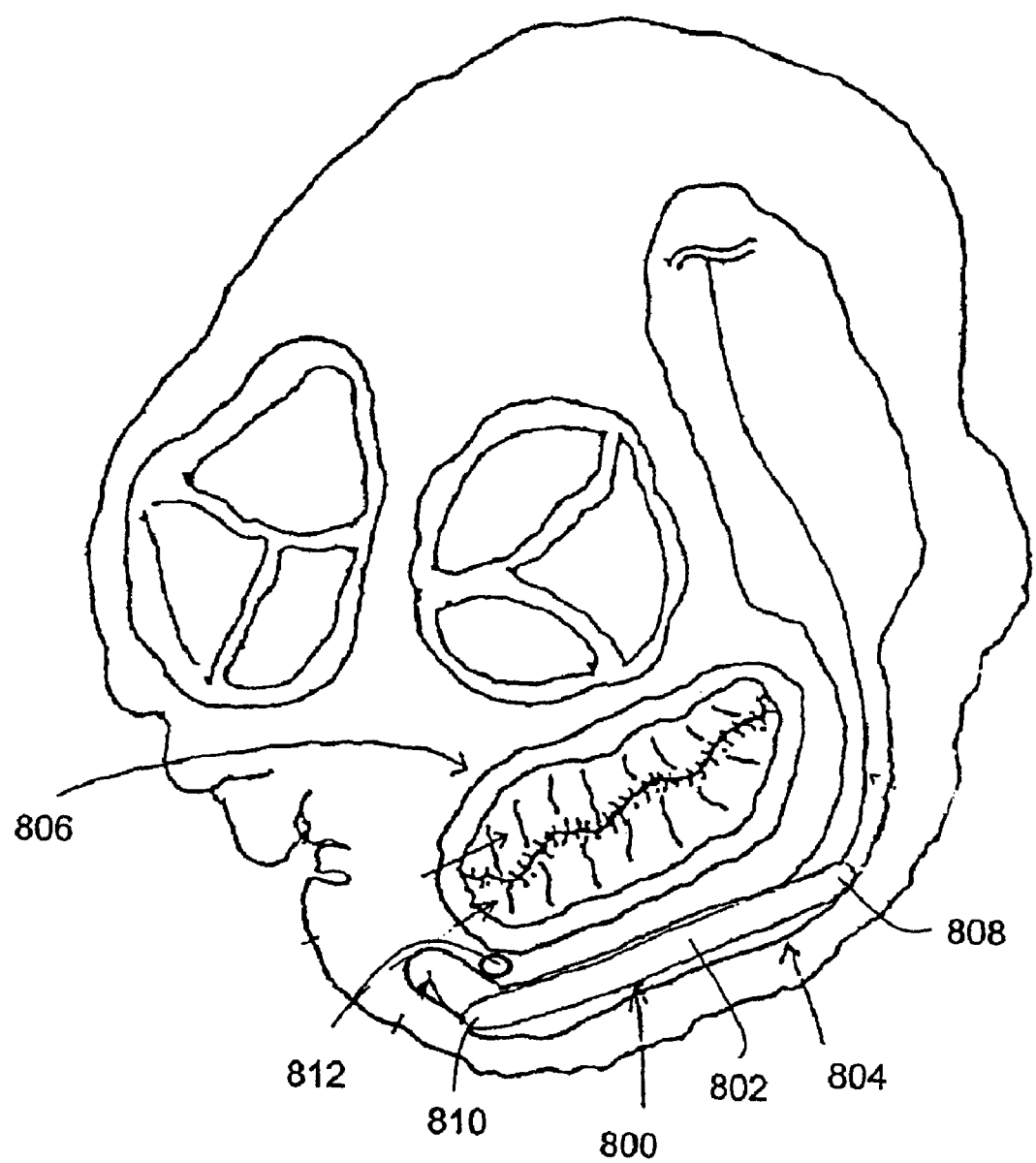
FIG. 30 is a schematic view of another embodiment demonstrating the method of this invention.

FIG. 30 shows yet another embodiment of the method of this invention. In this embodiment, a tissue shaping device 800 formed from a substantially straight rigid member 802 is disposed in the coronary sinus 804 to treat mitral valve regurgitation. When deployed as shown, the central portion of rigid member 802 exerts a remodeling force anteriorly through the coronary sinus wall toward the mitral valve 806, while the proximal and distal ends 808 and 810, respectively, of rigid member 802 exert posteriorly-directed forces on the coronary sinus wall. According to this invention, device 800 is disposed in relation to the circumflex artery 812 so that all of the anteriorly-directed forces from rigid member 802 are posterior to the crossover point between artery 812 and coronary sinus 804, despite the fact that distal end 810 of device 800 and a guidewire portion 814 are distal to the crossover point.

The device of FIG. 30 may also include a less rigid portion at the distal end 810 of member 802 to further eliminate any force directed toward the mitral valve distal to the crossover point. Further details of the device (apart from the method of this invention) may be found in U.S. patent application Ser. No. 10/112,354, published as U.S. Patent Appl. Publ. No. 2002/0183838, the disclosure of which is incorporated herein by reference.

Figure 31:
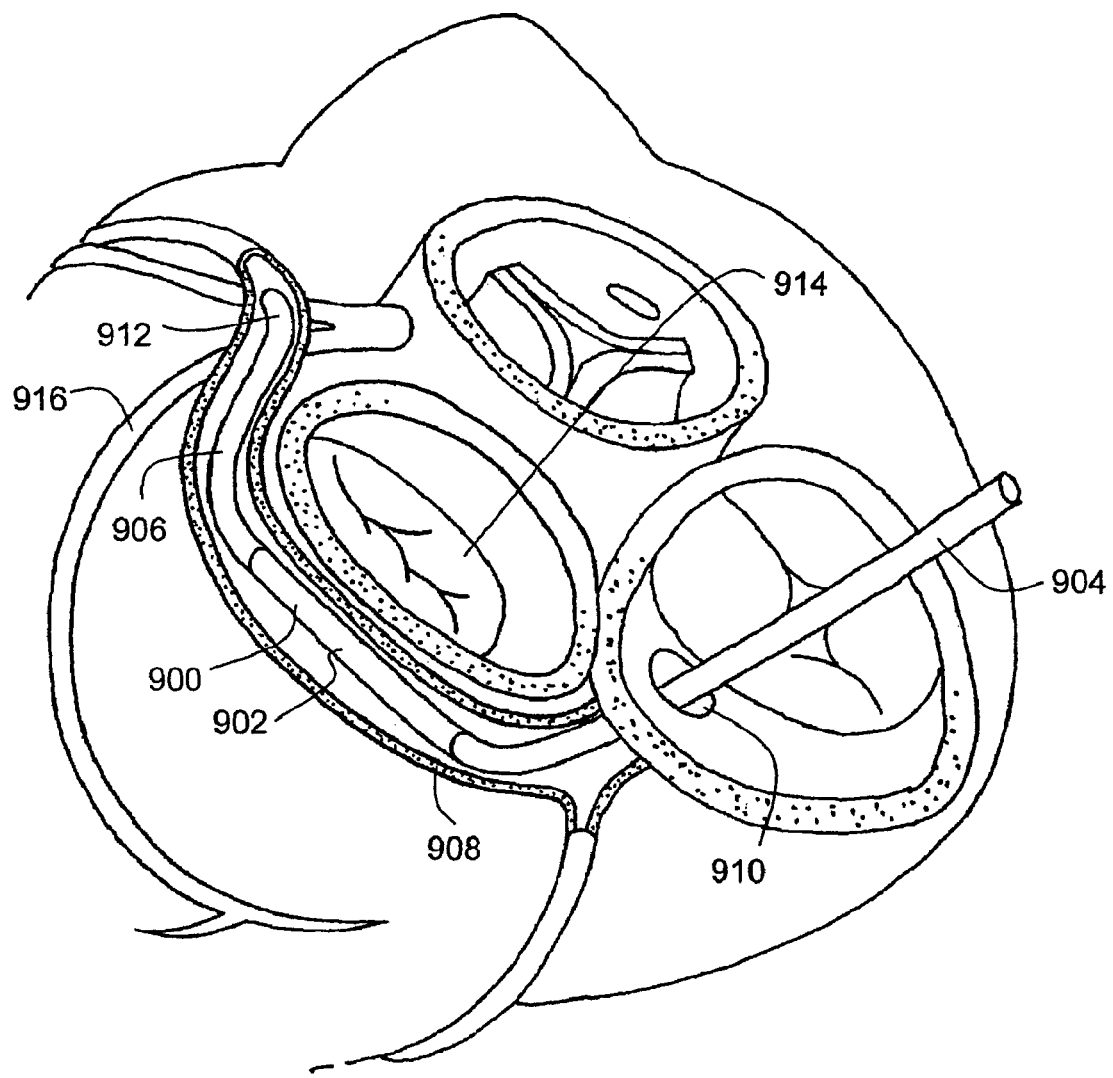
FIG. 31 is a schematic view of yet another embodiment demonstrating the method of this invention.

FIG. 31 shows another embodiment of the method of this invention. Device 900 has a substantially straight rigid portion 902 disposed between a proximal angled portion 904 and a distal angled portion 906 within coronary sinus 908. As shown, proximal angled portion 904 extends through the coronary sinus ostium 910 within a catheter (not shown). Distal angled portion 906 extends distally to a hooked portion 912 that is preferably disposed in the AIV.

To treat mitral valve regurgitation, the device's straight portion 902 reshapes the coronary sinus and adjacent tissue to apply an anteriorly directed force through the coronary sinus wall toward the mitral valve 914. Due to the device's design, this reshaping force is applied solely proximal to the crossover point between coronary sinus 908 and the patient's circumflex artery 916, despite the fact at least a part of the device's distal portion 906 and hooked portion 912 are disposed distal to the crossover point.

Other modifications to the inventions claimed below will be apparent to those skilled in the art and are intended to be encompassed by the claims.

What is claimed is:

1. A method of making a tissue shaping device comprising:
   removing material from a blank to form a connector and an integral anchor portion; and
   attaching a non-integral anchor portion to the integral anchor portion,
   wherein the integral anchor portion is a first integral anchor portion, the removing step further comprising removing material from the blank to form a second integral anchor portion, the connector being disposed between the first integral anchor portion and the second integral anchor portion, and wherein the non-integral anchor portion is a first non-integral anchor portion, the method further comprising attaching a second non-integral anchor portion to the second integral anchor portion.

2. The method of claim 1 wherein the first integral anchor portion comprises a crimp tube and the first non-integral portion comprises a flexible wire, the method further comprising disposing a portion of the flexible wire in the crimp tube.

3. The method of claim 1 wherein the blank has a substantially cylindrical cross-section, the removing step comprising removing a portion of the cylinder to leave a connector having a substantially semi-circular cross-section.

4. The method of claim 1 wherein the first and second anchor portions each comprises a crimp tube and the first non-integral anchor portion comprises a flexible wire, the method further comprising disposing a portion of the flexible wire in the first anchor crimp tube.

5. The method of claim 1 wherein the first and second integral anchor portions each comprises a crimp tube and the first and second non-integral anchor portions each comprises a flexible wire, the method further comprising disposing a portion of the first anchor flexible wire in the first anchor crimp tube and disposing a portion of the second anchor flexible wire in the second anchor crimp tube.

6. The method of claim 1 wherein the blank has a substantially cylindrical cross-section, the removing step comprising removing a portion of the cylinder to leave a connector having a substantially semi-circular cross-section.

* * * * *